US011186597B1

(12) United States Patent
Khedr et al.

(10) Patent No.: US 11,186,597 B1
(45) Date of Patent: Nov. 30, 2021

(54) METHOD OF EXTRACTING PHOSPHOLIPIDS FROM FISH ROE

(71) Applicant: King Abdulaziz University, Jeddah (SA)

(72) Inventors: Alaa Eldin M. Khedr, Jeddah (SA); Abdelsattar M Omar, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/357,095

(22) Filed: Jun. 24, 2021

(51) Int. Cl.
  *C07F 9/10* (2006.01)
  *C11B 1/10* (2006.01)
  *C11B 7/00* (2006.01)
  *C07C 69/587* (2006.01)
  *B01D 11/02* (2006.01)

(52) U.S. Cl.
  CPC ............... *C07F 9/103* (2013.01); *C11B 1/10* (2013.01); *C11B 7/0025* (2013.01); *C11B 7/0041* (2013.01); *B01D 11/02* (2013.01); *C07C 69/587* (2013.01)

(58) Field of Classification Search
  CPC ... C07F 9/103; C11B 1/02; C11B 1/10; C11B 7/0025; C11B 7/0041; C07C 69/587; B01D 11/02
  See application file for complete search history.

(56) References Cited

U.S. PATENT DOCUMENTS

| 4,814,111 | A  | * | 3/1989  | Kearns ...................... A23J 7/00 554/83 |
| 7,189,418 | B2 |   | 3/2007  | Hiratsuka |
| 8,206,739 | B2 |   | 7/2012  | Berge |
| 8,784,921 | B2 |   | 7/2014  | Koshikawa |
| 8,846,604 | B2 | * | 9/2014  | Hallaraker ............. A23K 50/60 514/1.1 |
| 9,718,759 | B2 |   | 8/2017  | Petrie |
| 10,704,011 | B2 |   | 7/2020  | Hoem |
| 10,993,925 | B2 |   | 5/2021  | Berger |
| 2010/0143571 | A1 | * | 6/2010  | Breivik ................... A23L 33/12 426/643 |

OTHER PUBLICATIONS

Folch, J., et al., A simple method for the isolation and purification of total lipides from animal tissues, Journal of Biological Chemistry, 226(1), pp. 497-509 (Year: 1957).*

Papadopoulos et al., "Validation and Application of a Protocol for the Extraction and Quantitative Analysis of Sphingomyelin in Erythrocyte Membranes of Patients with NAFLD", BioRvix, Preprint posted Apr. 21, 2021.

Tanaka et al., "Extraction of Phospholipids from Salmon Roe with Supercritical Carbon Dioxide and an Entrainer", J Oleo Sci. 2004, vol. 53, 417-424.

* cited by examiner

*Primary Examiner* — Yate' K Cutliff
(74) *Attorney, Agent, or Firm* — W & C IP

(57) ABSTRACT

Provided herein is a method to extract bioactive phospholipids from fish roe, particularly from salmon roe, providing an extraction solvent composition mixture of chloroform, ethanol, and isopropanol.

13 Claims, 16 Drawing Sheets

FIG. 1A
FIG. 1B
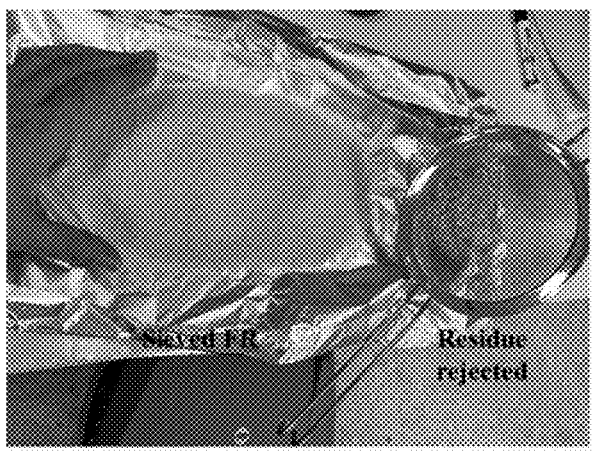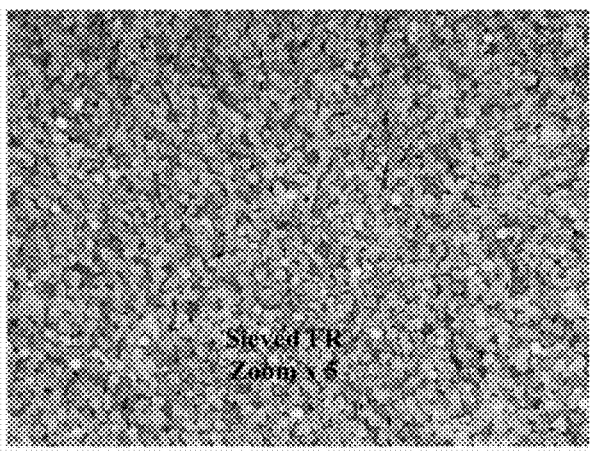
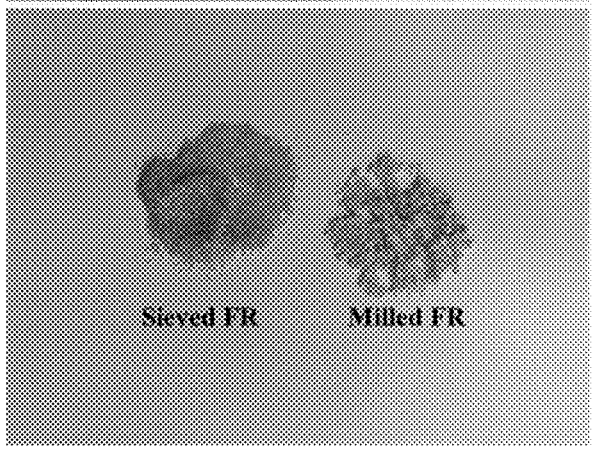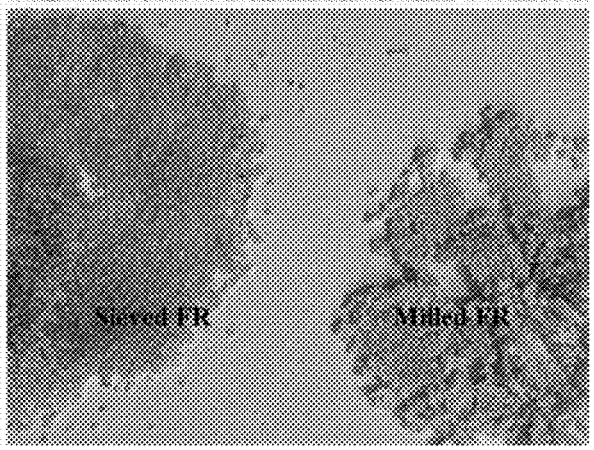
FIG. 1C
FIG. 1D

FIG. 11A
FIG. 11B
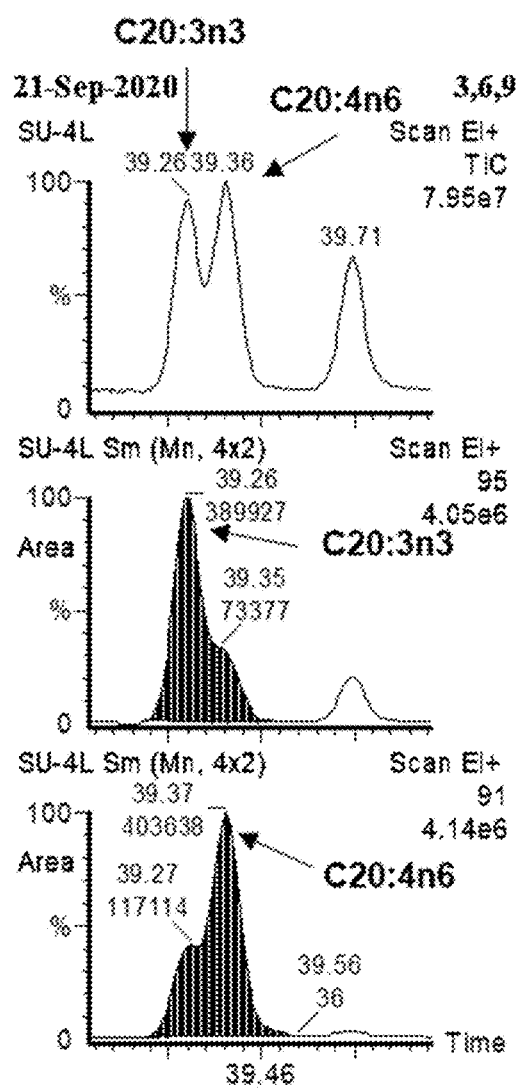
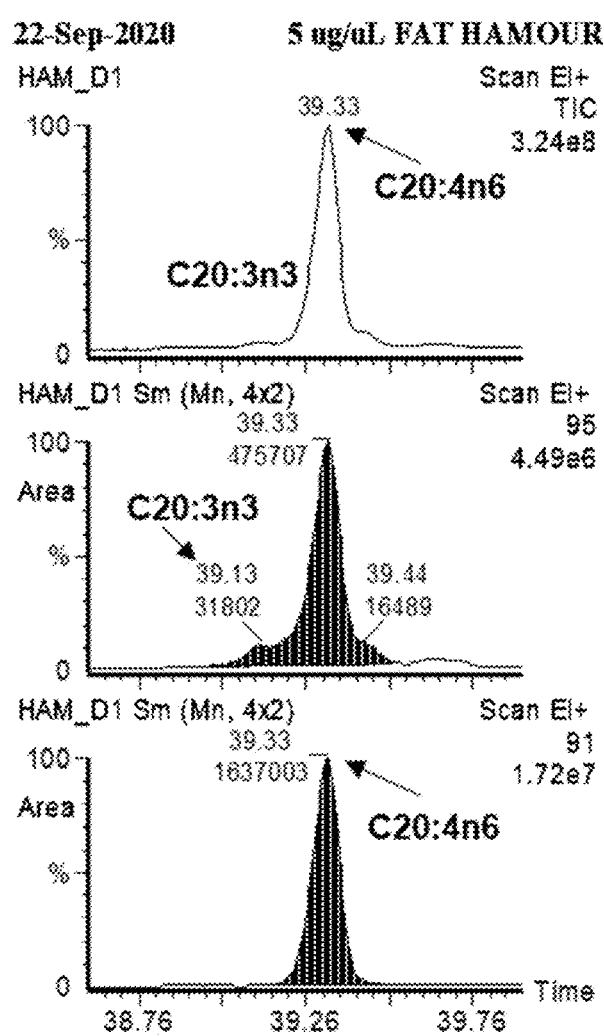

METHOD OF EXTRACTING PHOSPHOLIPIDS FROM FISH ROE

FIELD OF THE INVENTION

The disclosure provides a method of extracting phospholipids (PL) from fish roe. In particular, the present invention includes a method of extracting PL wax from freeze-dried fish roe powder. The extraction method includes blending of dried and frozen fish roe powder in the extraction solvent comprising chloroform, ethanol, and isopropanol.

BACKGROUND

Bioactive fatty acids are the primary component of lipids and play a crucial role in biological systems. A number of types of bioactive fatty acids have been identified, including fatty acids in free forms and/or bound forms such as cholesterol and phospholipids. Among those identified fatty acids, omega-3 fatty acids are often referred to as essential fatty acids for their functions in regulating human health. The two major health-promoting omega-3 polyunsaturated fatty acids are eicosapentaenoic acid (EPA) and docosahexaenoic acid (DHA). EPA and DHA are naturally found in certain cold-water fatty fish such as salmon, tuna, and mackerel. DHA has important structural and anti-inflammatory roles in the body. EPA also is beneficial for health as it serves as a precursor for prostaglandin-3, thromboxane-3, and leukotriene-5 eicosanoids [2]. A comprehensive review of their properties, sources, bioavailability, and relation to brain health has been discussed [1].

Similar to some essential amino acids, omega-3 fatty acids cannot be synthesized in the body and must be consumed from the diet or dietary supplements. Generally, the omega-3 fatty acids are provided in dietary supplements as free fatty acids, ethyl esters, or triglycerides and are inefficiently processed in the body. These non-polar ingredients can induce burping and discomfort and require increased amounts to be consumed to provide intended beneficial effects to compensate inefficient processing [1]. Although adequate amounts of omega-3 fatty acids can be obtained by including fish (e.g., salmon, tuna, etc.) in the diet, larger fish species are also known to contain high levels of mercury, polychlorinated biphenyls, dioxins, or other contaminants. Also, the source of these materials contains a variable content with some unwanted impurities. It is a concern to develop a preparation procedure that yields enough amount of lipids with a precise pattern. Moreover, the exact composition of such phospholipid-wax is not currently described or illustrated to have a stable composition pattern. The co-extracted materials from such matrixes, like plant or fish (soya bean, salmon roe, krill), are not analyzed or identified in a precise percentage. Also, no straightforward analysis or extracting procedure has been found to evaluate the potency and exact composition of the extracted phospholipid wax. Stability or spoilage of the extracted phospholipid products due to the excessive contained moisture in the products is also a concern. An exemplary conventional phospholipids extraction method is well described in U.S. Pat. No. 8,846,604 to Hallaraker, hereby incorporated as reference. However, most of the conventional extraction methods known in the art include one or more aqueous solution washing steps leading to lowering production yield as well as introducing moisture, thereby shortening the shelf-life of the products.

Thus, there is a need in the art for an improved phospholipids extraction method providing simple and effective isolation of phospholipids, which preferably include high levels of DHA and EPA in a well-preserved condition.

SUMMARY OF THE INVENTION

An object of the invention is a method of extracting phospholipids and bioactive materials from fish roe. The method includes an improved process for extracting and preparing phospholipids from fish roe, preferably from salmon roe, for use in pharmaceuticals, nutraceuticals, and functional foods. One of the advantageous features of the present invention is the use of a particular extraction solvent for quick isolation of the phospholipids without additional washes, thereby co-extracting polar bioactive materials in the final phospholipid extraction product. Elimination of the aqueous solution washing steps excludes the probability of partitioning of some lipid contents to the aqueous phase and thus causing the low extraction recovery. An additional feature includes the use of ethanol and isopropanol in the extraction solvent to minimize solvent-based toxicity.

One aspect of the disclosure provides a method of extracting omega-3 fatty acid-enriched bioactive materials from a fish or fish byproduct. The method involves contacting the fish or fish byproduct with a concentrated extraction solvent and directly purifying the phospholipids without additional washing procedures.

Another aspect of the disclosure provides a method for extracting one or more phospholipids, wherein the method comprises steps of collecting and freezing fish roe, drying and grinding the fish roe into a powder form, blending the fish roe with a solvent under conditions such that the one or more phospholipids are preferentially extracted to form a slurry comprising a polar lipid solution and biological residue material, and drying to produce isolated phospholipids under vacuum. The method includes a direct extract-and-dry process, which does not include a step of washing, particularly a washing step with a water-containing solution or by adding the aqueous solution to dilute the extraction solvent. In some embodiments, the extraction solvent includes 10-25 v/v % of isopropanol. In some embodiments, the extraction solvent includes 15-35 v/v % of ethanol. In some embodiments, the extraction solvent includes 30-65 v/v % of chloroform. In preferred embodiments, the extraction solvent comprises a mixture of chloroform, ethanol, and isopropanol in a 2:1:0.5 v/v ratio. In some embodiments, the fish roe may be selected from the group of seven species of fish roe, including hamour, tuna, mosa, sevruga beluga, bory, lump, and salmon roe. The fish roe used in the extraction is frozen at −80° C. for 12-24 hours. After the freezing procedure, the fish roe is dried in a lyophilizer at 0.05-0.01 mbar.

The preparation and characterization of lipid contents of fish roe extract of the present invention is intended for human use to help in improving psychomotor behavior, mental health, sexual libido, Alzheimer's, anxiety, and sleep disorder. The health impact of the unique PL-wax extract composition of PCs, EFAs, and specific bioactive materials may also be measured to adjust the extraction procedure described in detail below.

Additional features and advantages of the present invention will be set forth in the description of disclosure that follows, and in part, will be apparent from the description of may be learned by practice of the disclosure. The disclosure will be realized and attained by the compositions and methods particularly pointed out in the written description and claims hereof.

BRIEF DESCRIPTION OF THE DRAWINGS

FIG. 1A-D show (A) sieved form of hamour fish roe and filtered rejected residue (B) dried hamour fish roe in a sieved form (C) both sieved and milled fish roe, and (D) another view of the FIG. 1C of sieved and milled fish roe.

FIG. 11A-B show the integration of C20:3n3 and C20:4n6 in the calibration of the injected (A) standard solution and (B) hamour fish roe sample.

DETAILED DESCRIPTION

Figure 2:
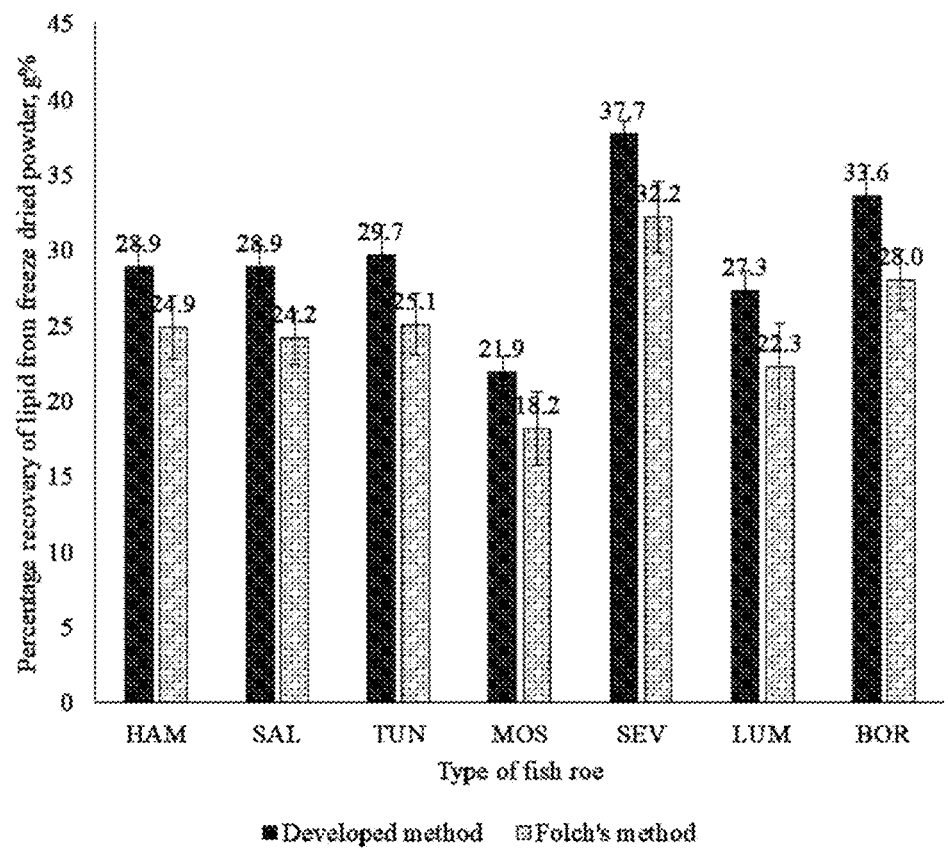
FIG. 2 shows a histogram of the percentage of lipid mass recovery from freeze-dried roe by applying the extraction method of the present invention and comparing the percentage of recovery with that of the Folch extraction method.
Figure 3A:
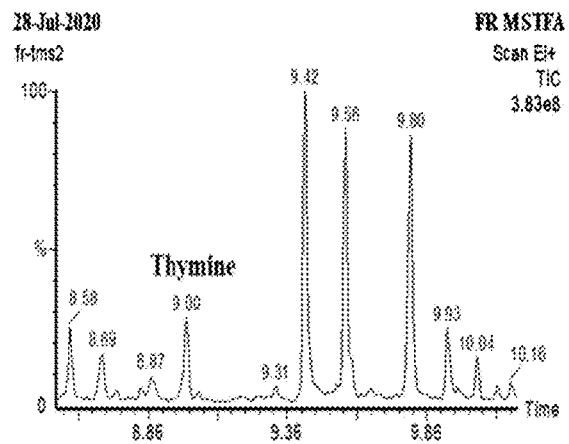
FIG. 3A-D show a representative TIC of MSTFA treated lipid extract obtained from Hamour roe with (A) thymine (B) hypoxanthine and adenine (C) pantothenic acid (D) glycerol, uracil, and cholesterol peaks.
Figure 3B:
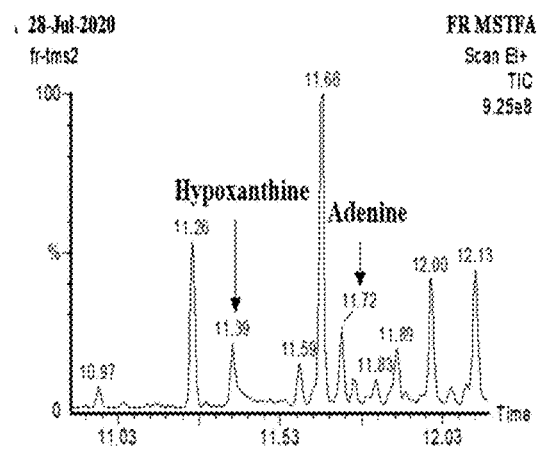
Figure 3C:
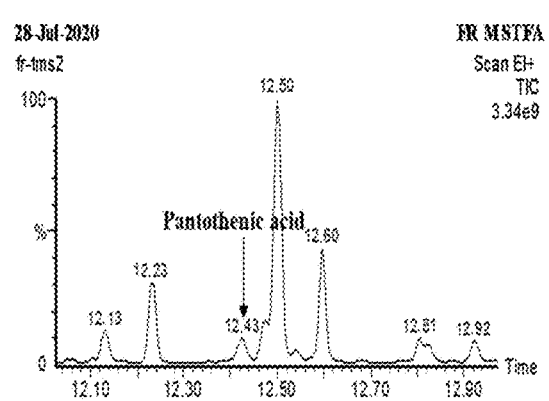
Figure 3D:
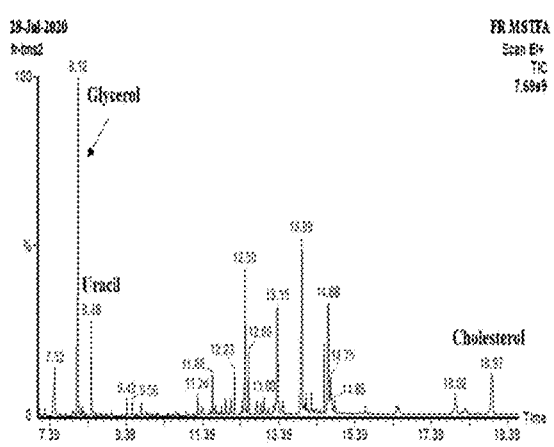

The preferred embodiments of the present disclosure are directed toward a method of extracting phospholipids containing bioactive fatty acids from fish roe. A preferred method includes a phospholipids extraction procedure where the fish roe is blended and extracted in a mixture of organic solvents comprising chloroform, ethanol, and isopropanol. The source material of the extracted phospholipids is fish roe, preferably salmon roe.

In some embodiments, the method of extracting phospholipids containing bioactive fatty acids from a fish or fish byproduct. The method involves contacting the fish or fish byproduct with a concentrated extraction solvent and directly purifying the phospholipids containing or surrounding bioactive fatty acids without additional washing procedures. The phospholipids may be obtained from fish or fish byproducts, such as internal fish organs, fish portions after processing, or fish roe. Any stages or types of fish roe, such as mature fish roe or immature fish roe, may be contemplated for the extraction method. In particular, hamour roe, salmon roe, tuna roe, mosa roe, sevruga sturgeon roe, lump roe, bory roe, or combinations thereof may be used for the present invention.

The bioactive fatty acids that are to be extracted in the present invention encompasses a range of structures, from simple saturated fatty acids to complex molecules derived from various biological compounds that are important for regulating physiological processes such as energy homeostasis, cell proliferation, metabolic homeostasis and in the regulation of inflammatory processes. The term, "fatty acid", as used herein, refers to an alkanoic acid or an alkanoic acid moiety (i.e., the residue left after formal removal of the acid hydrogen), where the fatty acid includes at least about nine or ten carbon atoms. Non-limiting examples of fatty acids include decanoic acid (10:0), undecanoic acid (11:0), 10-undecanoic acid (11:1), lauric acid (12:0), cis-5-dodecanoic acid (12:1), tridecanoic acid (13:0), myristic acid (14:0), myristoleic acid (cis-9-tetradecenoic acid, 14:1), pentadecanoic acid (15:0), palmitic acid (16:0), palmitoleic acid (cis-9-hexadecenoic acid, 16:1), heptadecanoic acid (17:1), stearic acid (18:0), elaidic acid (trans-9-octadecenoic acid, 18:1), oleic acid (cis-9-octadecanoic acid, 18:1), nonadecanoic acid (19:0), eicosanoic acid (20:0), cis-11-eicosenoic acid (20:1), 11,14-eicosadienoic acid (20:2), heneicosanoic acid (21:0), docosanoic acid (22:0), erucic acid (cis-13-docosenoic acid, 22:1), tricosanoic acid (23:0), tetracosanoic acid (24:0), nervonic acid (24:1), pentacosanoic acid (25:0), hexacosanoic acid (26:0), heptacosanoic acid (27:0), octacosanoic acid (28:0), nonacosanoic acid (29:0), triacosanoic acid (30:0), trans vaccenic acid (trans-1'-octadecenoic acid, 18:1), tariric acid (octadec-6-ynoic acid, 18:1), and ricinoleic acid (12-hydroxyoctadec-cis-9-enoic acid, 18:1) and ω3, ω6, and ω9 fatty acyl residues such as 9,12,15-octadecatrienoic acid (α-linolenic acid) [18:3, ω3]; 6,9,12,15-octadecatetraenoic acid (stearidonic acid) [18:4, ω3]; 11,14,17-eicosatrienoic acid (di-homo-.alpha.-linolenic acid) [20:3, ω3]; 8,11,14,17-eicosatetraenoic acid [20:4, ω3], 5,8,11,14,17-eicosapentaenoic acid [20:5, ω3]; 7,10,13,16,19-docosapentaenoic acid [22:5, ω3]; 4,7,10,13,16,19-docosahexaenoic acid [22:6, ω3]; 9,12-octadecadienoic acid (linoleic acid) [18:2, ω6]; 6,9,12-octadecatrienoic acid (7-linolenic acid) [18:3, ω6]; 8,11,14-eicosatrienoic acid (dihomo-γ-linolenic acid) [20:3 ω6]; 5,8,11,14-eicosatetraenoic acid (arachidonic acid) [20:4, ω6]; 7,10,13,16-docosatetraenoic acid [22:4, ω6]; 4,7,10,13,16-docosapentaenoic acid [22:5, ω6]; 6,9-octadecadienoic acid [18:2, ω9]; 8,11-eicosadienoic acid [20:2, ω9]; 5,8,11-eicosatrienoic acid (Mead acid) [20:3, ω9]; trans-10,cis-12 octadecadienoic acid; cis-10,trans-12 octadecadienoic acid; cis-9,trans-11 octadecadienoic acid; and trans-9,cis-11 octadecadienoic acid. The acyl residues of a fatty acid moiety can also be conjugated, hydroxylated, epoxidized, and/or hydroxyepoxidized acyl residues.

In preferred embodiments, omega-3 fatty acids are extracted from fish or fish byproducts. An "omega-3 fatty acid" refers to a polyunsaturated fatty acid that has the final double bond in the hydrocarbon chain between the third and fourth carbon atoms from the methyl end of the molecule or moiety. Non-limiting examples of omega-3 fatty acids include Δ-5,8,11,14,17-eicosapentaenoic acid (EPA), Δ-4,7,10,13,16,19-docosahexaenoic acid (DHA) and Δ-7,10,13,16,19-docosapentanoic acid (n-3 DPA). In some embodiments, the extracted omega-3 fatty acids, including EPA and DHA that are bound to phospholipids (i.e., phospholipid molecule having an omega-3 fatty acid residue at the sn1 position, the sn2 position or both) and has a superior bioavailability for the dietary supplement use.

The term "phospholipid" as used herein refers to a glycerol phosphate with an organic headgroup such as choline, serine, ethanolamine or inositol and either one or two fatty acids esterified to the glycerol backbone. Phospholipids include, but are not limited to, phosphatidylcholine, phosphatidylethanolamine, phosphatidylserine and phosphatidylinositol as well as corresponding lysophospholipids. The term "phospholipid wax" or "PL wax" refers to a mass of phospholipids that is a solid at room temperature (~23° C.). A PL wax as described herein can have a melting point interval in the range of about 28° C. to about 65° C. Some PL waxes can have a melting point interval in the range of about 28° C. to about 38° C., about 28° C. to about 35° C., about 28° C. to about 34° C., about 35° C. to about 65° C., about 40° C. to about 60° C., about 45° C. to about 55° C., or about 55° C. to about 65° C. Other PL waxes can have a melting point interval in the range of about 50° C. to about 60° C., about 40° C. to about 50° C., about 30° C. to about 40° C., about 30° C. to about 38° C., about 30° C. to about 35° C., or about 30° C. to about 33° C. The melting point interval can be an interval of about 2, about 3, about 4, about 5, about 7, or about 10° C. within one of the recited ranges. The PL wax can be pliable and the solid can be dissolvable in oils such as vegetable or fish oils.

As used herein, a "PL oil" refers to a viscous oil derived from a PL wax where the PL wax is further processed or purified to provide the viscous oil, rich in phospholipids. In some embodiments, the term "phospholipids" and "phospholipid containing fatty acids" may be interchangeably used and refer to one or more naturally occurring phospholipids incorporating fatty acids (e.g., omega-3 fatty acids).

One aspect of the disclosure provides a method for extraction one or more phospholipids and comprises steps of collecting and freezing fish roe, drying and grinding the fish roe into a powder form, blending the fish roe with a solvent under conditions such that one or more phospholipids are preferentially extracted to form bioactive phospholipids and biological residue materials, and drying to produce isolated phospholipids under vacuum. The method includes a direct extract-and-dry process, which does not include a step of washing, particularly a washing step with a water-containing solution or by adding the aqueous solution to dilute the extraction solvent.

In preferred embodiments, the extraction solvent comprises a mixture of chloroform, ethanol, and isopropanol in various volume per volume ratio. In some embodiments, the extractions solvent includes 10-25 v/v. % of isopropanol. In some embodiments, the extraction solvent includes 15-35 v/v % of ethanol. In some embodiments, the extraction solvent includes 30-65 v/v % of chloroform. For example, chloroform, ethanol, and isopropanol may be in a 2:1:0.5 v/v ratio. By determining the % of extracted types of fatty acids or bioactive materials, the ratio of chloroform to ethanol or to isopropanol may be adjusted accordingly. In some embodiments, the ratio of chloroform to ethanol may be about 3:1 to 1:1 v/v. The ratio of ethanol to isopropanol may be about 3:1 to 1:1. In addition, the ratio of chloroform to isopropanol, in some embodiments, may be 6:1 to 3:1. In other embodiments, the solvent may further include other food-safe solvents selected from the group consisting of n-hexane, cyclohexane, liquid propane, acetone, ethyl acetate, and combinations thereof. In some embodiments, the extraction method may further include a supercritical fluid extraction with carbon dioxide. However, in preferred embodiments, methanol may not be included in the extraction solvent. Further, in some embodiments, the extraction method does not include washing of the phospholipids with an aqueous solution or diluting of the extraction solvents with water during purification. In yet another embodiment, the extraction solvent may comprise any types of protic solvent such as ethanol, isopropanol, and chloroform, n-butanol, n-propanol, isopropanol, methanol, or combinations of diluted protic solvent.

In some embodiments, the fish roe may be selected from the group of seven species of fish roe, including hamour, tuna, mosa, sevruga beluga, bory, lump, and salmon roe. The fish roe used for the extraction is frozen at −80° C. for 12-24 hours. After the freezing procedure, the fish roe is dried in a lyophilizer at 0.05-0.01 mbar. In preferred embodiments, the phospholipids are extracted from salmon roe. In some embodiments, the phospholipids and bioactive materials are extracted from hamour roe.

In some embodiments, the bioactive fatty acid and bioactive residue materials of the extracts may comprise 1-99% of omega-3 fatty acids. In such cases, the omega-3 moieties of the phospholipids extracts are eicosapentaenoic acid (EPA), docosahexaenoic acid (DHA) or combinations thereof. The ratio of EPA to DHA of extracts may be 10:1 to 1:5 on a molar basis. In some embodiments, the extracts and compositions comprise greater than about 40-95% phospholipid compounds in phospholipids weight per total weight of the extract. The ratio or amounts of fatty acids or phospholipids may preferably be determined by an analytical method selected from the group consisting of gas chromatography (GC), high-performance liquid chromatography (HPLC), GC-mass spectrometry (GC-MS), nuclear magnetic resonance (NMR), or other suitable methods as is known in the art. The extracted phospholipids or bioactive fatty acids may also be blended or washed with other composition materials or solvents. For example, the extracted phospholipids may be blended or washed with other lipids compositions, in which the phospholipids containing omega-3 fatty acid moiety are about 1-60% w/w of the total composition, with the remaining 99-40% w/w of the composition being other free fatty acids, omega-3 glycerides, esters or a combination thereof. In other embodiments, the phospholipids extract may further comprise other agents, such as flavoring agents, sweeteners, emulsifiers, nutritional supplements, and deodorants.

The methods and uses described herein may further include treating a subject in need thereof, comprising the steps of administering the bioactive phospholipids formulation in an oral delivery vehicle, food product, nutritional supplement, dietary supplement, or functional food comprising the phospholipid or bioactive fatty acids formulation to the subject. In some embodiments, the administration is oral, topical, parenteral, enteral, transdermal, intradermal, intraocular, intravitreal, sublingual, or intravaginal, and may preferably comprise an effective amount of the composition.

Example 1

Phospholipid Extraction and Chemical Analysis

The materials used for the phospholipid extraction analysis include: Fresh salmon (SAL) and red lump roe were purchased from Benfumat, Barcelona, Spain. Other fresh Hamour (HAM), Tuna (TUN), Mosa (MOS), Sevruga Beluga (Sturgeon, SEV), and Bory (BOR) roe were purchased fresh from the local fish market. Loratadine (LOR), ≥98%, was purchased from Merck, Darmstadt, Germany. 2,4-dihydroxypyrimidine (uracil, URA)>98%, hypoxanthine (HYP), >99%, and 1H-purin-6-amine (adenine, ADE), >98%, were purchased from Fluorochem Ltd., Hadfield, UK. Cholesterol (CHO), >95%, was purchased from Sigma- Aldrich, Shinagawa, Tokyo, Japan. Thymine (THY), >98%, and pantothenic acid (vitamin B5, VB5), ≥98%, were purchased from TargetMol, Wellesley Hills, Boston, USA. Glycerol (GLY), >98%, and N-methyl-N-trimethylsilyl-trifluoroacetamide (MSTFA), 99.8% w/v, were purchased from Sigma-Aldrich (St. Louis, Mo., USA). Supelco® 37 fatty acid methyl esters (FAME) standard mixture was purchased from Sigma-Aldrich Co. (Saint Louis, Mo., USA). The screw-capped (PTFE/silicon) 1 ml autosampler total recovery vials (12×32 mm) were purchased from Waters (Milford, Mass., USA). Myristic acid ethyl ester (internal standard) was prepared in our laboratory by acid esterification in $H_2SO_4$/Et-OH. These esters were tested for purity by GC-MS (>99.6%). Synthetic lipid standards were purchased from Avanti Polar Lipids, Inc. (AL, USA), and the purity of each was more than 99.0%: 19:0_19:0 PC, 17:0_17:0 PC, 17:0 LPC, 19:0 LPC, 17:0_17:0 PE, and 15:0_15:0 PE. Chloroform, acetonitrile, methanol, ethanol, and isopropanol were of HPLC grade. All solvents were purchased from Sigma-Aldrich (Sigma-Aldrich Chemie GmbH, Steinheim, Germany). Ammonium hydroxide solution, 25% w/v as ammonia, was purchased from Fluka Sigma-Aldrich (Riedel-de Haen, Germany).

The solvent mixture used is referred to as; Solvent 1: $CHCl_3$:MeOH, 2:1, v/v, Solvent 2: $CHCl_3$:DMSO, 1:1, v/v, used for reconstitution to keep PE soluble at room temperature during analysis. Solvent 3: $CHCl_3$:ethanol:isopropanol (2:1:0.5, v/v), extraction solvent. GC-MS system conditions applied for the analysis of biogenic materials GC-MS, Clarus 500 GC/MS (PerkinElmer, Shelton, Conn.) was used. The software controller/integrator was TurboMass, version 5.4.2.1617 (PerkinElmer). An Optima-1 GC capillary column, 100% dimethyl polysiloxane (30 m×0.25 mm ID×0.25 µm df, Macherey-Nagel GmbH& Co. KG, Duren, Germany) was used. The carrier gas was helium (purity 99.9999%) was adjusted at a flow rate of 0.9 ml/min. Source (EI+) temperature, 200°; GC line temperature, 220°; electron energy, 70 eV; and trap emission, 100°. Oven program included initial temperature, 900 (hold 5 min), to 2800 (rate 20° C./min, hold 10 min), increased to 305° (rate 22.0° C./min, hold 2.5 min); injector temperature, 280°; MS scan, 40 to 350 m/z; injection volume was 1.0 µl, the split ratio was 50:1. GC-MS, Clarus 500 GC/MS (PerkinElmer, Shelton, Conn.) was used. The software controller/integrator was TurboMass, version 5.4.2.1617 (PerkinElmer). Teknokroma TR-CN100 GC capillary column (60 m×0.25 mm ID×0.20 mdf) was used (Teknokroma, Analitica SA, Barcelona, Spain). The carrier gas was helium (purity 99.9999%) was adjusted at a flow rate of 1.2 ml/min. Source (EI+) temperature, 210°; GC line temperature, 220°; electron energy, 70 eV; and trap emission, 100°. Oven program included initial temperature, 900 (hold 1 min), to 180° C. (rate 2.8.0° C./min, hold 2.0 min), increased to 215° C. (rate 2.0° C./min, hold 0 min); injector temperature, 225° C.; MS scan, 40 to 350 m/z; injection volume was 1.0 µl, the splitless-split mode was applied (split ratio 5% at 0 min, and 45% at 0.15 min).

LC-MS system used for the characterization of PL is described herein: Targeted phospholipids were characterized by using Agilent 6320 liquid chromatography—ion trap mass spectrometer (LC-IT-MS). The LC-MS system was controlled with ChemStation software (Rev. B.01.03 SR2 (204)), and 6300 series trap control version 6.2 Build No. 62.24 (Bruker Daltonik GmbH). The IT-MS parameters were: capillary voltage, 4300 V; nebulizer, 36 psi; drying gas, 12 L/min; desolvation temperature, 325° C.; and max accumulation time, 200 ms. The MS scan range was 50-950 m/z. The positive precursor ions were extracted and scanned auto-fragmented at a positive scan mode.

LC-MS system and method of use for the quantification of PLs is described herein: the quantitative analysis was completed using an Agilent high-performance liquid chromatography coupled with Agilent-6460 triple quad mass spectrometer (LC-QqQ-MS) (Agilent Technologies, Palo Alto, Calif., USA). The ionization source was the electrospray ionization mass system. An Agilent 1200 HPLC system was equipped with a quaternary pump, an autosampler, and a column compartment. The system was controlled by MassHunter software (version B.03.01, Build 3.1.346.0). The MS conditions: gas temperature, 325° C.; gas flow rate, 12 L/min; nebulizer pressure; 38 psi, and capillary voltage, 4300 V. Positive scan mode was applied, 100-950 m/z. For HPLC conditions, the chromatographic separation was performed on Agilent Eclipse Plus C18, 4.6×100 mm column, 3.5 µm (Agilent Technology, Palo Alto, Calif., USA). The column temperature was maintained at 40±2° C. Three solvent reservoirs were used. Line A; water, methanol, 750:250 mL, v/v, mixed with 4 mL ammonium hydroxide 25%, line B; methanol:chloroform, 950:50 mL, v/v, mixed with ammonium hydroxide 25%, line C; methanol:chloroform, 800:200 mL, v/v. The pump was programmed to deliver solvents using gradient mode, as shown in TABLE 1.

TABLE 1

Elution program downloaded to the HPLC pump

| Time, min | % A | % B | % C | Flow, mL/min |
|---|---|---|---|---|
| 0 | 65 | 35 | 0 | 0.5 |
| 5 | 65 | 35 | 0 | 0.5 |
| 8 | 30 | 70 | 0 | 0.4 |
| 37 | 12 | 88 | 0 | 0.4 |
| 40 | 6 | 94 | 0 | 0.4 |
| 50 | 6 | 94 | 0 | 0.4 |
| 70 | 1 | 99 | 0 | 0.4 |
| 75 | 0 | 100 | 0 | 0.4 |
| 76 | 0 | 0 | 100 | 0.5 |
| 80 | 0 | 0 | 100 | 0.5 |
| 81 | 65 | 35 | 0 | 0.5 |

The collected Fresh fish roe sacs were washed with deionized water, empty sac with a sharp knife, the eggs were collected in a glass container, washed with water using a sieve. The freshly washed fish roe was left to stand in the refrigerator at −80° C. for one day. The solid freeze fish roe was then transferred to Lyophilizer equilibrated at −60° C. and a maximum vacuum of 0.05-0.01 mbar. The dried fish roe was ground smoothly, manually using porcelain mortar to separate any skin membrane layer. The bulk powder was left inside the dissector over activated silica gel 20-60 µm particle size for seven days under vacuum at room temperature. The collected amount of dried fish roe was sieved to separate the fish roe from skin residue, as shown in FIG. 1A-D. The sieved fish roe was then kept at −80° C. until the extraction process.

To extract phospholipids, the composition of the extraction solvent of $CHCl_3$:ethanol:isopropanol (2:1:0.5, v/v) was used. About 25 g of dried fish roe was blended for 5 min using an electric blender (a machine used as a coffee blender). A weight of 500 mg of this finely powdered fish roe was mixed with 8 mL extraction solvent composed of $CHCl_3$:ethanol:isopropanol (2:1:0.5, v/v) in a 15-mL screw-capped glass test tube. (The ratio of FR powder, as gram, to extraction solvent volume, is 0.6±0.02 g to 8 mL). This mixture was vortexed for 2 min, sonicated for 20 min in an ultrasonic bath at room temperature, centrifuged at 5000 rpm for 10 min. The clear supernatant was separated by decantation to a 25 mL round bottom flask. This yellowish extract was evaporated in a rotary evaporator until dryness at 35° C. under vacuum and running chilled water (0° C.). The extraction procedure was repeated using seven types of fish roe including, Hamour (HAM), Salmon (SAL), Tuna (TUN), Mosa (MOS), Sevruga sturgeon (SEV), Lump (LUM), and Bory (BOR).

As an experimental control, the commonly used Foch method was used. The same freezing and powdering procedures were followed but using $CHCl_3$:MeOH, 2:1, v/v, as the extraction solvent. After the extraction process and drying, the following items were completed;
i) Calculation of the LIPID mass yield and precision as milligram per gram of dried FR powder.
ii) GC-MS analysis of lipid mass for characterization of active biogenic materials.
iii) GC-MS analysis for the determination of esterified fatty acid content.
iv) LC-IT-MS analysis to characterize the major phospholipids (PLs).
v) LC-QqQ-MS quantitative analysis of the major phospholipids (PLs).
vi) Calculation of the precision values of the estimated amounts of active biogenic materials, major PLs, and EFAs.

The standard solutions were prepared separately to give a concentration of 1 mg/mL. Cholesterol and loratadine were dissolved in chloroform. Adenine, thymine, uracil, hypoxanthine, and pantothenic acid were dissolved in methanol containing 0.1%, w/v, ammonia solution with sonication aid. Separately a stock solution of adenine, thymine, uracil, hypoxanthine, and pantothenic acid was prepared in methanol to obtain a 20 ng/μL for each analyte, and a concentration of 50 ng/μL of both cholesterol and glycerol were prepared separately.

The extracted fat mass was dissolved in chloroform to give a concentration of 10 mg/mL. A volume of 25 μL of each fat solution, 10 mg/mL, was transferred to the autosampler vial, mixed with 50 μL in solution, 10 ng/μL, dried with nitrogen gas, mixed with 50 μL MSTFA with the aid of vortex for 2 sec., the vials were caped, heated at 80° C. for 10 min, cooled, and a volume of 1 μL was injected for GC-MS analysis applying the MRM mode. The same procedure was repeated using a sample lipid concentration of 100 mg/mL, to analyze the targeted analytes at existed a low concentration.

Six concentration levels were prepared in an autosampler vial by mixing 10, 20, 30, 40, 50, and 60 μL from each internal standard solution. A volume of 50 μL from the internal standard solution, 10 ng/μL, was added to each concentration level, mixed and dried with a gentle stream of nitrogen gas. A volume of 50 μL MSTFA was added, mixed with the aid of vortex for two sec., the vials were caped, heated at 80° C. for 10 min, cooled, and a volume of 1 μL was injected for GC-MS analysis. The concentration of each analyte in the final injected solution is listed in TABLE 2.

TABLE 2

The concentration of the analytes in the prepared calibration levels (L)

| Stock, ng/μL | SIR, m/z | Rt, min | Analyte | Concentration, ng/μL | | | | | |
|---|---|---|---|---|---|---|---|---|---|
| | | | | L1 | L2 | L3 | L4 | L5 | L6 |
| 50 | 205 | 8.12 | Glycerol | 10 | 20 | 30 | 40 | 50 | 60 |
| 20 | 241 | 8.48 | Uracil | 4 | 8 | 12 | 16 | 20 | 24 |

TABLE 2-continued

The concentration of the analytes in the prepared calibration levels (L)

| Stock, ng/μL | SIR, m/z | Rt, min | Analyte | Concentration, ng/μL | | | | | |
|---|---|---|---|---|---|---|---|---|---|
| | | | | L1 | L2 | L3 | L4 | L5 | L6 |
| 20 | 255 | 9.00 | Thymine | 4 | 8 | 12 | 16 | 20 | 24 |
| 20 | 265 | 11.39 | Hypoxanthine | 4 | 8 | 12 | 16 | 20 | 24 |
| 20 | 264 | 11.72 | Adenine | 4 | 8 | 12 | 16 | 20 | 24 |
| 20 | 291 | 12.43 | Pantothenic acid, Vit B5 | 4 | 8 | 12 | 16 | 20 | 24 |
| 50 | 129 | 18.97 | Cholesterol | 10 | 20 | 30 | 40 | 50 | 60 |
| 10 | 382 | 18.32 | Loratadine, InSt | 10 | 10 | 10 | 10 | 10 | 10 |

Trans-methylation of lipid extract for GC-MS analysis of EFA is described herein. The extracted lipid mass was analyzed for the composition of esterified fatty acid composition using gas chromatography-mass spectrometry. A weight of 100 mg lipid mass was dissolved in 10 mL $CHCl_3$:methanol, 2:1, v/v, 10 mg/mL. A volume of 25 μL from lipid solution (10 mg/mL) was transferred to 2-ml glass vial, dried with nitrogen gas at room temperature. The residue was reconstituted in 50 μL of toluene, mixed with 100 μL of 0.5 M methanolic potassium hydroxide, vortexed, and maintained at 550 for 25 min using a hot air oven. The vial was cooled, and a volume of 250 μL water containing 20% glacial acetic acid was added and vortexed for 10 s. The reaction mixture was mixed with 25 μL internal standard solution (myristic acid ethyl ester, 50 ng/μL), and vortexed. This solution was extracted with n-hexane (250 μL×3 times). The n-hexane, supernatant layer, was withdrawn using a Pasteur pipette and transferred to a 1-ml total recovery vial leaving the aqueous layer (lower), dried with a gentle stream of nitrogen gas at room temperature, reconstituted in 50 μL $CH_2Cl_2$ and a volume of 1.0 μl was injected for GC-MS analysis. The analysis procedure was repeated six times for each lipid extract.

Preparation of calibration solution for GC-MS analysis of EFA in FR extract is described herein: Microliter TLC syringes from Perkin Elmer were used for the quantitative transfer of RS-Supelco® 37-FAME solution (Perkin Elmer Instruments, Australia, syringe with a replaceable luer-tip, 5, 10, and 100 μl capacity). The labeled concentrations of reference standard Supelco® 37 FAME solutions were 200, 400, or 600 ng/μL, as specified for each fatty acid in the leaflet. A stock solution was prepared by diluting 100 μL to 1 mL with $CH_2Cl_2$. This stock solution was used to prepare six serial dilutions, spanning the range as shown in TABLE 3-4. An equivalent volume from each level was mixed with the internal standard solution (50 ng/μL) injected for GC-MS analysis.

TABLE 3

Concentration levels of the prepared calibration solution mixture containing 2, 4, or 6% of FAME with 25 ng/μL myrestic acid ethyl ester as internal standard

| | Concentration, ng/μL | | |
|---|---|---|---|
| Level | Labeled 2% | Labeled 4% | Labeled 6% |
| L1 | 0.4 | 0.8 | 1.2 |
| L2 | 1.0 | 2.0 | 3.0 |
| L3 | 2.0 | 4.0 | 6.0 |
| L4 | 3.0 | 6.0 | 9.0 |
| L5 | 4.0 | 8.0 | 12.0 |
| L6 | 10.0 | 15.0 | 30.0 |

TABLE 4

The concentration of the selected FAMEs in the prepared calibration levels

| EFA | Quantifier Trace, m/z | $t_R$, min | Concentration, ng/uL * | | | | | |
|---|---|---|---|---|---|---|---|---|
| | | | Level 1 | Level 2 | Level 3 | Level 4 | Level 5 | Level 6 |
| C12:0 | 74 | 14.15 | 0.8 | 2 | 4 | 6 | 8 | 15 |
| C14:0 | 74 | 19.16 | 0.8 | 2 | 4 | 6 | 8 | 15 |
| C14:1 | 55 | 20.87 | 0.4 | 1 | 2 | 3 | 4 | 10 |
| C15:0 | 74 | 21.65 | 0.4 | 1 | 2 | 3 | 4 | 10 |
| C16:0 | 74 | 24.14 | 1.2 | 3 | 6 | 9 | 12 | 30 |
| C16:1 | 55 | 25.45 | 0.4 | 1 | 2 | 3 | 4 | 10 |
| C18:0 | 74 | 28.88 | 0.8 | 2 | 4 | 6 | 8 | 15 |
| C18:1n9t | 55 | 29.63 | 0.4 | 1 | 2 | 3 | 4 | 10 |
| C18:1n9c | 55 | 29.93 | 0.8 | 2 | 4 | 6 | 8 | 15 |
| C18:2n6c | 67 | 31.79 | 0.4 | 1 | 2 | 3 | 4 | 10 |
| C18:3n6 | 67 | 33.12 | 0.4 | 1 | 2 | 3 | 4 | 10 |
| C18:3n3 | 67 | 34.01 | 0.4 | 1 | 2 | 3 | 4 | 10 |
| C20:1 | 55 | 34.38 | 0.4 | 1 | 2 | 3 | 4 | 10 |
| C21:0 | 74 | 35.73 | 0.4 | 1 | 2 | 3 | 4 | 10 |
| C20:2 | 67 | 36.45 | 0.4 | 1 | 2 | 3 | 4 | 10 |
| C20:3n6 | 67 | 37.95 | 0.4 | 1 | 2 | 3 | 4 | 10 |
| C20:3n3 | 79 | 38.99 | 0.4 | 1 | 2 | 3 | 4 | 10 |
| C20:4n6 | 79 | 39.31 | 0.4 | 1 | 2 | 3 | 4 | 10 |
| C22:1n9 | 55 | 39.42 | 0.4 | 1 | 2 | 3 | 4 | 10 |
| C20:5n3 | 79 | 41.81 | 0.4 | 1 | 2 | 3 | 4 | 10 |
| C22:6n3 | 79 | 48.14 | 0.4 | 1 | 2 | 3 | 4 | 10 |

* Each concentration level contains internal standard, myrestic acid ethyl ester, 25 ng/μL.

Preparation of standard PLs solutions is described herein. Separately, a concentration of 1 mg/mL of each internal standard (IS), and each calibrant (CA) was prepared in Solvent 1. The PE standards were dissolved with the aid of warming at 40° C. The final concentration of each PL stock solution was equal to 1000 ng/μL. Two separate PLs solution mixtures were prepared, including; the calibrant PLs mixture and internal standard mixture. The internal standards were include, 17:0_LPC (IS1, m/z 510.3), 19:0_19:0 PC (IS2, m/z 818.6) and 15:0_15:0 PE (IS3, m/z 664.5) for the drawing the calibration curve of 19:_LPC (C1, m/z 538.4), 17:0_17:0 PC (C2, m/z 762.6), and 17:0_17:0 PE (C3, m/z 720.5), respectively.

A volume of 0.5 mL of each IS1, IS2, and IS3 (1000 ng/μL, each) was mixed in 2.0 mL vial and diluted to 5 mL with solvent 2 (3.5 mL solvent-2, was added) to give a final concentration of 100 ng of each IS. This IS solution mixture was further diluted to give a concentration of 20 ng/μL. A stock solution containing three PLs calibrant was prepared in solvent 1 to give a concentration of 250 ng/μL of each, C1, C2, and C3. A volume of 250 μL of each calibrant (1000 ng/μL) was mixed in 2-mL vial and diluted to 1 mL with solvent 1 to give a stock a calibrant solution mixture containing 250 ng/μL, of each C1, C2, C3. A serial dilution of PLs calibration mixture was prepared, spanning a range of 1.0 to 300 ng/μL. A volume of 50 μL of each PLs calibration concentration was mixed with 50 μL of IS solution mixture. The final concentration of each IS was 10 ng/μL with PLs calibration concentration ranged from 0.5 to 150 ng/μL. A volume of 5 μL of each concentration level was injected for LC-QqQ-MS. The positive precursor ion of each PLs compound, internal standards, and calibrants, were extracted and the peak area was integrated. The calibration curve of each PLs representative group was constructed by plotting the peak area ratio of C1(m/z 538.4):IS1(m/z 510.3), C2(m/z 762.6):IS2(m/z 818.6), and C3(m/z 720.5):IS3(m/z 664.5) versus the concentration as ng/μL. The retention time of IS1, IS2, IS3, C1, C2, and C3 was 30.7, 72.7, 43.9, 37.4, 60.0, 46.9 min, respectively.

Preparation of PLs in FR extract for LC-MS analysis is described herein. To a glass vial 15-mL (amber glass), a weight of 100 mg of prepared extracted lipid mass was transferred and dissolved in 10 mL chloroform:dimethyl sulfoxide, 1:1, v/v, to give a concentration of 10 mg/mL. A volume of 50 μL from this solution was mixed with 50 μL of PLs-internal standard solution mixture, 20 ng/μL, and mixed with vortex aid. A volume of 5 μL was injected for LC-IT-MS and LC-QqQ-MS analysis. The concentrated samples were re-analyzed after making suitable dilutions.

Example 2

Here we describe a novel method for extraction of fats from fish roe to achieve the following main objectives: (a) To obtain the highest fat extraction rate from fish roe with acceptable precision, (b) to obtain accurate and precise analysis results of major phospholipids, esterified fatty acids, and bioactive materials, (c) to obtain a lipid extract safe for oral administration to help improve human psychomotor behavior and memory, (d) to profile the lipid composition and bioactive materials in seven types of fish roe.

To date, Folch's method is the most applicable procedure for the extraction of lipids from a wide range of biological specimens including, liver, muscle, plasma, and plant tissues [19]. Folch used a mixture of chloroform:methanol, 2:1, v/v to extract bulk lipids, followed by washing the polar constituents with water. Herein, we used dried samples and omitted the purification step to keep the final extract's polar bioactive material. Bligh and Dyer extraction procedures have been recommended to extract food materials with high water content reached 80% [20]. However, the present invention does not follow such procedures to minimize the amount of water co-extraction and to avoid the chance of microbial growth. In preferred embodiments, ethanol and isopropanol in combination with chloroform are used to provide several advantageous features, including; (a) ethanol and isopropanol are less toxic solvent than methanol that is used in extraction solvents of others, (b) to exclude the probability of partitioning of some lipid contents to the aqueous phase, and subsequent low extraction recovery (c) to exclude the negative impact of moisture on the stability of lipid mass, and (d) to minimize the chance of microbial growth due to moister.

Herein an efficient extraction method targeting the PLs and some bioactive materials from fish roe previously freeze-dried and powdered is described. The addition of isopropyl alcohol to the extraction solvent significantly improved the recovery rate compared to the Folch method. The best value of recovery percentage was obtained when using isopropanol, in a range of 14 to 25%. We preferred to use an extraction solvent containing 14% isopropanol to get lipid extract quickly dried using a rotary evaporator under vacuum.

The direct extraction of fish roe was not expressive since it gives an immensely fluctuated % recovery of lipid mass and subsequently fluctuated assay results of targeted analytes. The size of fish roe usually is variable and the size of the fish eggs varies from one species to another, so the surface subjected to extraction with the solvent mixture is also variable. Exposure to ultrasound shocks gives different results according to the thickness and area of the membrane coated with eggs. Accordingly, it was necessary to crush the eggs as much as possible into small, dry ground particles to increase the surface area exposed to the extraction solvent when mixing Tear off the lining membrane of the eggs to allow the extraction of constituents inside the eggs, as shown in FIG. 1A-D.

TABLE 5 and FIG. 2 show the percentage recovery and precision of lipid mass extracted from powdered freeze-dried fish roe applying the method of present invention and a control (Folch) extraction method, n=6. The developed method improved the yield % by 4.7±0.71%, matching with Folch's procedure. The highest lipid mass content was found in SEV, 37.7±2.11 g %, followed by BOR, 33.6±1.97 g %. Relatively, the lipid mass content in TUN, SAL, and LUM was approximately equal. However, MOS FR showed the lowest lipid mass %, 21.6±1.02 g %. Percentage recovery and precision of lipid mass extracted from powdered freeze-dried fish roe applying the developed and Folch extraction methods, n=6. The result of subtracting the % percentage recovery value resulting from the invented method from the Folch's method.

TABLE 5

Percentage recovery and precision of lipid mass extracted from powdered freeze-dried fish roe applying the developed and Folch extraction methods, n = 6

| Ex. No. | % Recovery of lipid mass from freeze-dried powder, as g % ± SD | | Difference, g %* |
|---|---|---|---|
| | Developed method | Folch's method | |
| HAM | 28.9 ± 1.37 | 24.9 ± 2.11 | 4.0 |
| SAL | 28.9 ± 1.38 | 24.2 ± 1.74 | 4.7 |
| TUN | 29.7 ± 2.01 | 25.1 ± 2.05 | 4.6 |
| MOS | 21.9 ± 1.02 | 18.2 ± 2.44 | 3.7 |
| SEV | 37.7 ± 0.88 | 32.2 ± 2.33 | 5.5 |
| LUM | 27.3 ± 1.34 | 22.3 ± 2.87 | 5.0 |
| BOR | 33.6 ± 1.97 | 28.0 ± 2.02 | 5.6 |

*The result of subtracting the % percentage recovery value resulting from the invented method from Folch's method.

A volume of 8 mL extraction solvent was found suitable for the maximum recovery of lipid content from 500±50 mg dried powdered fish roe. Table 6 showed the percentage recovery of extracted lipid mass from different weights of powdered freeze-dried fish roe using 8 mL solvent composed of chloroform:ethanol:isopropanol (2:1:0.5, v/v), n=3. The calculated statistical F-value between the values obtained from 500 mg as compared to 1000 mg was 0.9387, at df=5. This value showed that both data series have unequal variances. Moreover, the t-test, assuming unequal variances, showed a significant difference between the two data sets, t-calculated, 0.0108, at df of 10, and the critical t-value tail value is 2.228. The calculated statistical F-value between the values obtained from 500 mg vs. 700 mg was 0.8473, at df=5, F critical value is 0.1980. This value showed that both data series have unequal variances. Moreover, the t-test, assuming unequal variances, showed a significant difference between the two data set, t-calculated=0.0108, at df=10, the critical t-value tail value=2.228.

TABLE 6

The percentage recovery of extracted lipid mass from different weights of powdered freeze-dried fish roe using 8 mL solvent composed of chloroform:ethanol:isopropanol (2:1:0.5, v/v), n = 3

| FR | 150 mg FR | 250 mg FR | 500 mg FR | 700 mg FR | 1000 mg FR | 1500 mg FR |
|---|---|---|---|---|---|---|
| | | | % Recover ± SD | | | |
| HAM | 29.2 ± 1.80 | 28.4 ± 1.77 | 28.9 ± 1.37 | 29.2 ± 1.17 | 28.2 ± 4.22 | 27.1 ± 5.44 |
| SAL | 28.7 ± 1.01 | 28.8 ± 1.00 | 28.9 ± 1.38 | 28.7 ± 0.77 | 28.5 ± 3.01 | 27.5 ± 3.22 |
| TUN | 29.2 ± 1.73 | 29.9 ± 1.11 | 29.7 ± 2.01 | 29.8 ± 0.66 | 30.7 ± 3.81 | 27.9 ± 6.09 |
| MOS | 22.3 ± 0.07 | 21.9 ± 0.54 | 21.9 ± 1.02 | 22.1 ± 2.00 | 22.2 ± 3.33 | 20.0 ± 6.30 |
| SEV | 37.9 ± 0.30 | 37.4 ± 2.05 | 37.7 ± 2.11 | 36.5 ± 2.40 | 37.1 ± 3.88 | 35.5 ± 6.55 |
| LUM | 27.0 ± 1.80 | 27.1 ± 1.45 | 27.3 ± 1.34 | 27.4 ± 1.79 | 27.0 ± 4.06 | 25.5 ± 5.04 |
| BOR | 33.9 ± 2.20 | 33.6 ± 2.05 | 33.6 ± 1.97 | 33.4 ± 2.03 | 33.8 ± 4.08 | 31.8 ± 6.47 |

Figure 4:
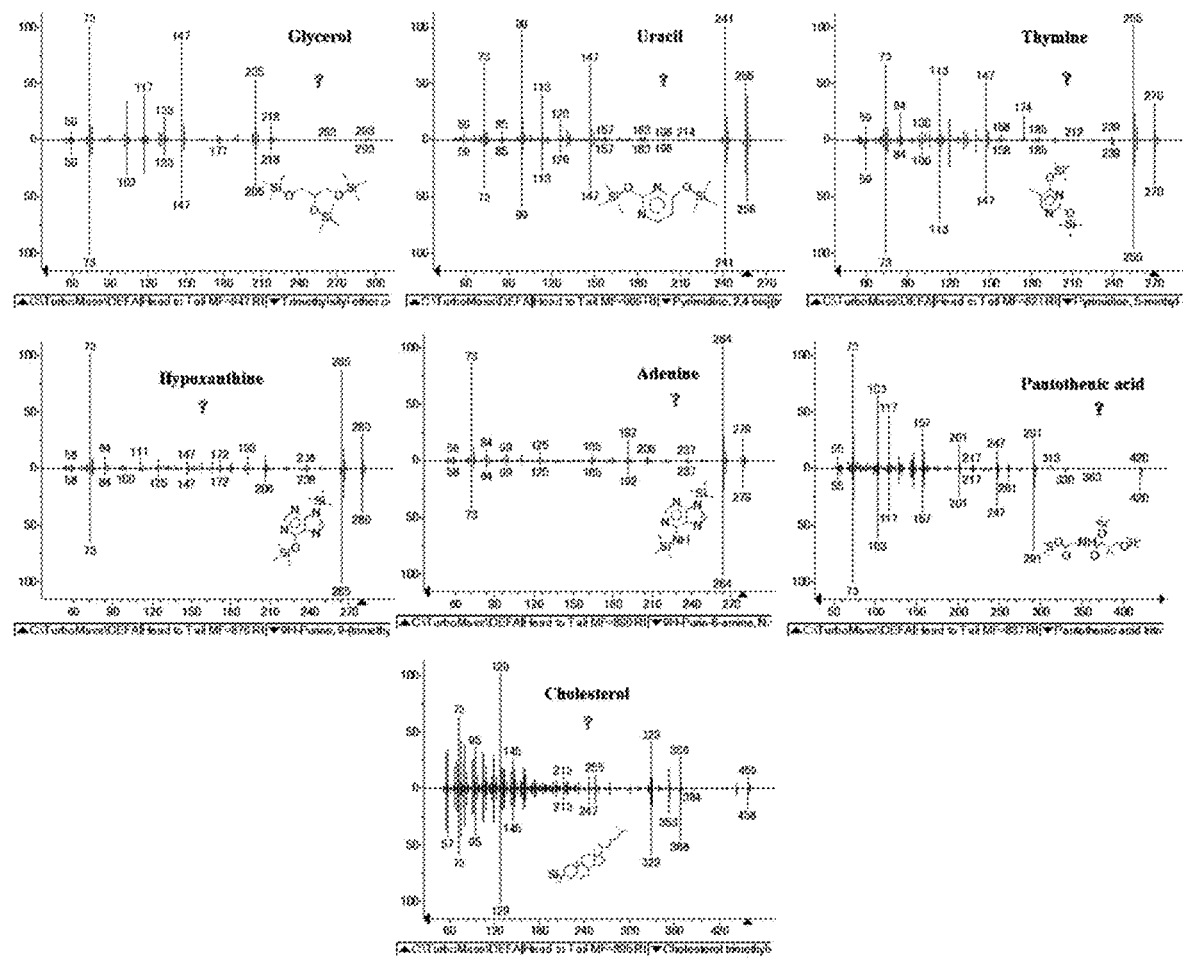
FIG. 4 represents identified compounds versus the matched compound of the NIST2008 database.
Figure 5:
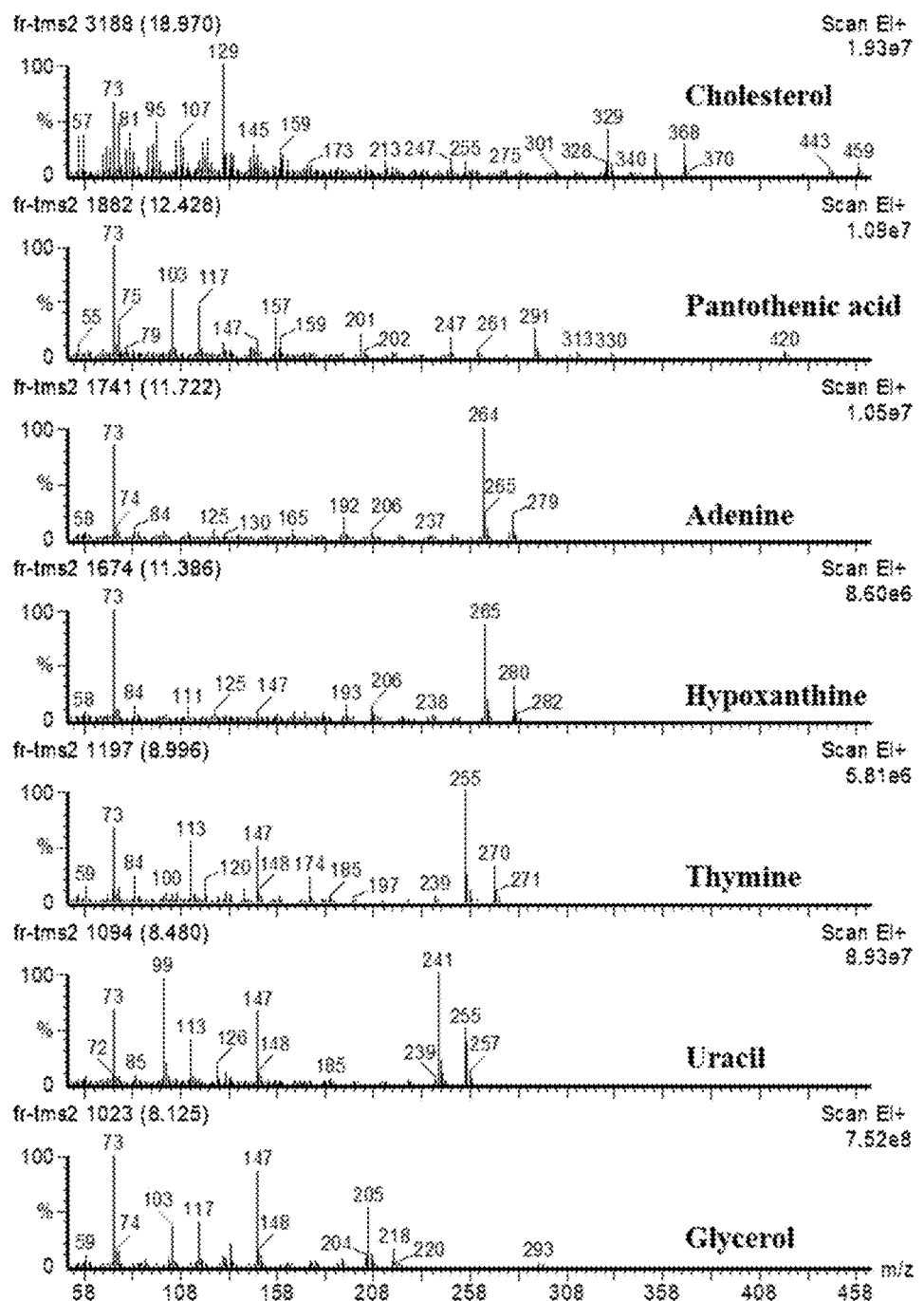
FIG. 5 shows EI-MS spectra of characterized bioactive entities found in Hamour roe extract.

The obtained lipid mass was investigated for bioactive materials such as glycerol (GLY), uracil (URA), thymine (THY), hypoxanthine (HYP), adenine (ADE), pantothenic acid (vitamin B5, VB5), and cholesterol (CHO), using GC-MS. A suitable concentration of the fish roe extract was prepared, followed by reacting with MSTFA at 80° C. for 10 min in dichloromethane. The GC-MS chromatogram of the lipid extract showed many peaks corresponding to fatty acids and phosphate ion ($PO_4$) as TMS derivatives. Glycerol-TMS was the major compound. Also, uracil, thymine, hypoxanthine, adenine, pantothenic acid (vitamin B5), and cholesterol were identified with the aid of the NIST2008 database. FIG. 3A-D show representative total ion chromatograms (TIC) of MSTFA treated lipid extract obtained from hamour roe. Moreover, the reference standard materials were derivatized with MSTFA, analyzed by GC-MS, and matched with the bioactive materials for further confirmation. FIG. 4-5 showed the MS confirmed compounds. These bioactive materials were quantified in the lipid extract of five types of fish roe extract using loratadine as an internal standard (InSt). Analytes were quantified at the most abundant m/z peak (trace ion) for maximum MS sensitivity (single-ion monitoring). The calibration curve was drawn by the relative peak area of trace ion of the internal standard (loratadine) to the peak area of the corresponding trace ion of the analyte (Y-values) versus the labeled concentration (X-values). Microsoft Excel was used to calculate the calibration parameters, including the regression coefficient (r), intercept (a), and response factor (b), as described in TABLE 7.

Khedr and Al Ahdal (2018) described the EFA content in fish roe applying Foch's extraction procedure [23]. Herein we describe the determination of EFA content in the obtained foe extract applying an improved extraction method. The extracted lipid from seven types of fish roe (FR) was treated with methanolic potassium hydroxide to obtain the methyl esters of esterified fatty acids, followed by GC-MS analysis. The EFAs detected in the lipid extract were characterized and confirmed by the NIST2008 database and Supelco® 37 FAME standard. The analyzed FR samples showed twenty-one fatty acid-methyl esters primarily. A minor amount corresponding to other FAs was ignored from the quantification process.

Figure 8:
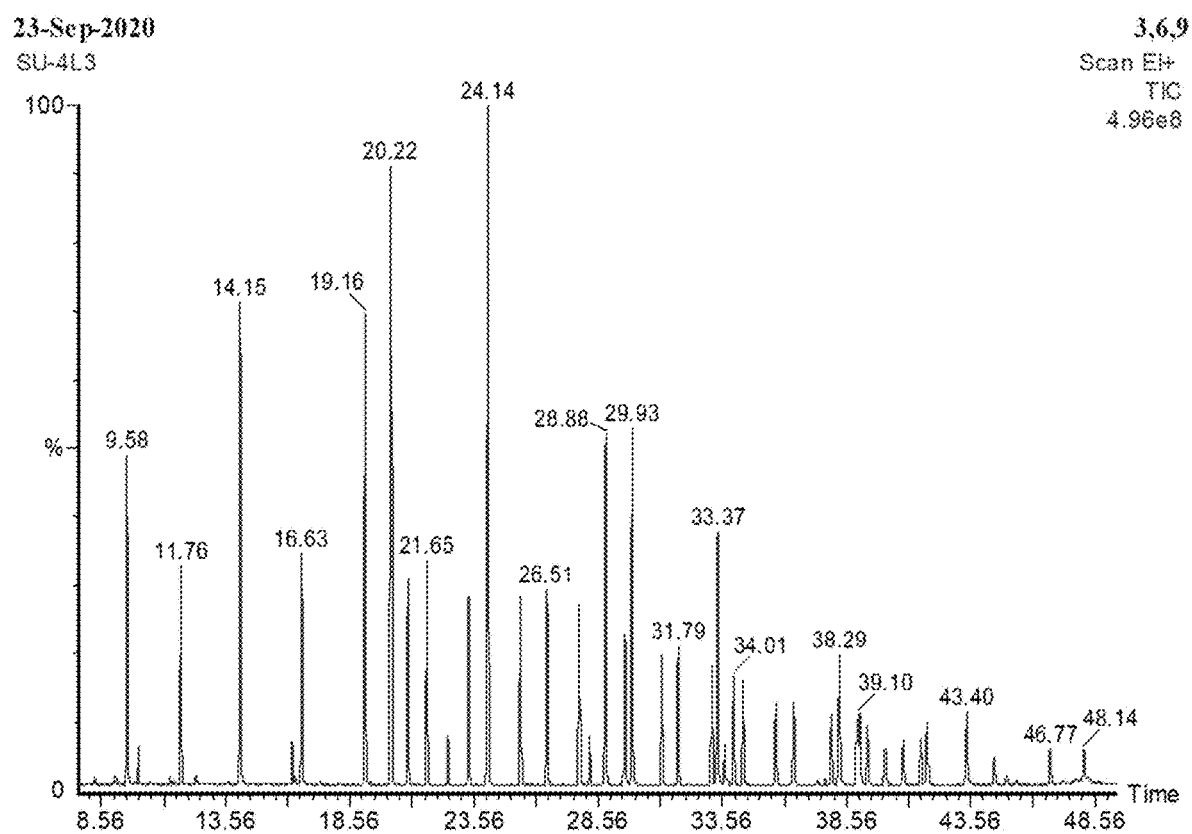
FIG. 8 shows GC-MS chromatogram of Supelco® 37 FAME standard mixture, level 4.

In FIG. 8, the GC-MS total ion chromatogram (TIC) of the standard FAME mixture, 50-350 m/z is shown. Samples were analyzed by applying MS-scan mode. The targeted EFA was quantified by integrating the peak area of extracted

TABLE 7

Calibration data of GC-MS analyzed bioactive compounds

| A compound as TMS derivative | Trace, m/z | Retention time, min | Regression coefficient, r | Intercept, a | Slope, b |
|---|---|---|---|---|---|
| 2,4-Bis(trimethylsilyl)uracil | 147 | 8.12 | 0.9954 | −0.2114 | 0.5654 |
| 2,4-Bis(trimethylsilyl)thymine | 241 | 8.48 | 0.9991 | −0.3554 | 1.4552 |
| Hypoxanthine di-TMS | 255 | 9.00 | 0.9978 | 0.0114 | 3.2470 |
| N-6,9-Bis(trimethylsilyl)adenine | 265 | 11.39 | 0.9998 | −0.1458 | 0.5529 |
| Pantothenic acid tri-TMS | 264 | 11.72 | 0.9968 | −1.0544 | 2.2723 |
| Cholesterol TMS ether | 103 | 12.43 | 0.9989 | −0.3053 | 0.2570 |
| 2,4-Bis(trimethylsilyl)uracil | 129 | 18.97 | 0.9999 | 0.0220 | 0.5516 |

Figure 6:
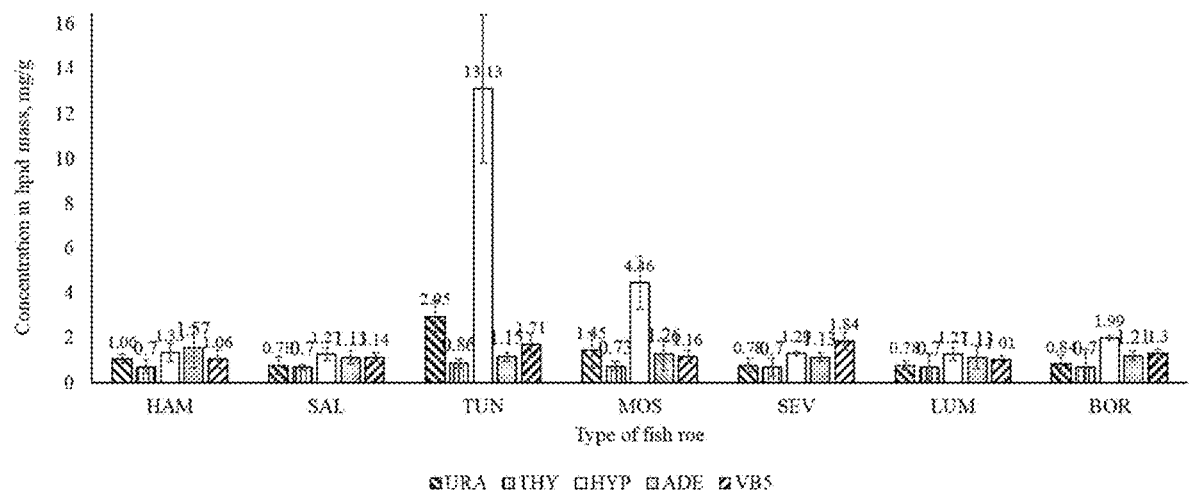
FIG. 6 shows the concentration of bioactive materials in seven types of fish roe extract.
Figure 7:
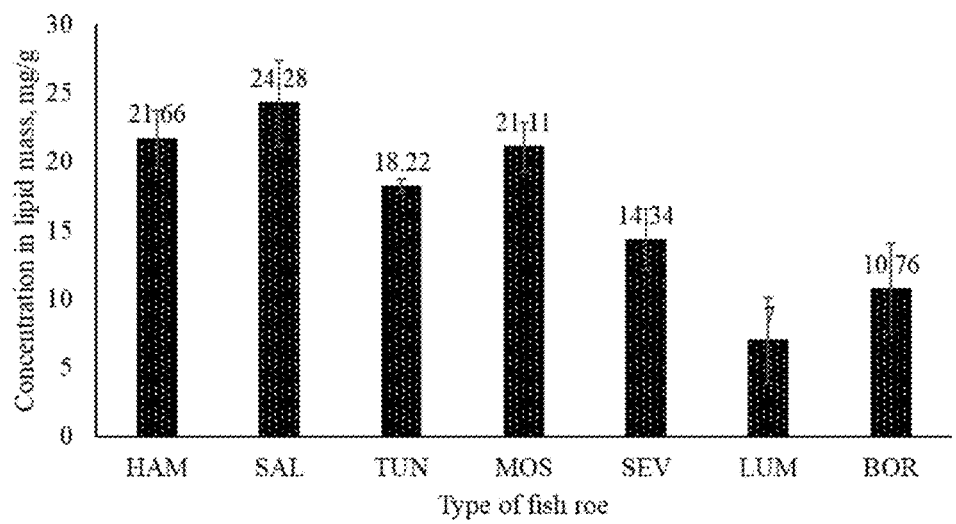
FIG. 7 shows the concentration of cholesterol in seven types of fish roe extract.

The calibration curves were linear, with a regression coefficient close to unity. The assay results of the bioactive materials showed that glycerol concentration was variable and not characteristic because of high standard deviation (concentrations ranged from 1.5 to 16 mg/g). FIG. 6-7 and TABLE 8 show the concentration of the five bioactive materials in the extracted lipid mass, labeled with the standard deviation values. Tuna and Mosa roe showed the highest content of hypoxanthine, 13.13±3.3, and 4.46±1.2 mg/g, respectively. The total concentration of the five bioactive materials, except GLY and CHO was relatively highest in TUN and MOS roe extract, 19.8 and 9.1 mg/g, respectively. Cholesterol was existed in the lowest amount, relatively, in LUM and BOR, 7.0±3.1 and 10.7±3.3 mg/g, respectively. However, the highest CHO content was found in SAL roe, 24.28±3.1 mg/g.

ion chromatogram using the most abundant m/z peak (trace ion). TABLE 4 shows the trace, m/z, and the selected twenty-one FAME's retention time. A sixteen FAMEs, as included in the Supleco® FAME solution, were ignored from quantification because of their absence or existed in a meager amount in the analyzed samples. Samples that showed a high concentration of the selected analytes were re-analyzed after preparing a suitable dilution, 2 to 10-fold, to obtain a reasonable GC-MS response within the corresponding calibration range. The calibration curves were drawn by constructing the relative peak area of each FAME to myrestic acid ethyl ester as the internal standard versus the nominated concentration as ng/µL. The calibration curves were linear within the working standard concentration, as shown in TABLE 9, and the regression coefficient value was close to unity.

TABLE 8

The concentration of bioactive materials in seven types of fish roe extract

| | Concentration, mg/g lipid mass ± SD | | | | | | |
|---|---|---|---|---|---|---|---|
| Analyte | HAM | SAL | TUN | MOS | SEV | LUM | BOR |
| Uracil | 1.06 ± 0.7 | 0.78 ± 1.0 | 2.95 ± 2.6 | 1.48 ± 3.4 | 0.78 ± 2.2 | 0.78 ± 0.4 | 0.84 ± 1.4 |
| Thymine | 0.70 ± 0.2 | 0.70 ± 0.4 | 0.86 ± 0.7 | 0.73 ± 0.8 | 0.70 ± 0.3 | 0.70 ± 0.2 | 0.70 ± 0.4 |
| Hypoxanthine | 1.33 ± 0.3 | 1.27 ± 0.3 | 13.13 ± 3.3 | 4.46 ± 1.2 | 1.29 ± 0.4 | 1.27 ± 0.6 | 1.99 ± 0.8 |
| Adenine | 1.57 ± 0.9 | 1.13 ± 0.3 | 1.15 ± 0.2 | 1.26 ± 0.7 | 1.13 ± 0.2 | 1.13 ± 0.5 | 1.21 ± 0.2 |
| Pantothenic acid | 1.06 ± 0.4 | 1.14 ± 0.2 | 1.71 ± 0.5 | 1.16 ± 0.3 | 1.84 ± 0.4 | 1.01 ± 0.2 | 1.30 ± 0.2 |
| Total concentration | 5.72 | 5.02 | 19.80 | 9.06 | 5.74 | 4.89 | 6.04 |
| Cholesterol | 21.66 ± 2.1 | 24.28 ± 3.1 | 18.22 ± 0.5 | 21.11 ± 1.8 | 14.34 ± 2.2 | 7.00 ± 3.1 | 10.76 ± 3.3 |

TABLE 9

Calibration data of FAME

| Retention time, min | EFA | Regression co-efficient, r | Intercept, a | Slope, b |
|---|---|---|---|---|
| 14.33 | C12:0 | 0.9995 | −0.045 | 0.168 |
| 19.38 | C14:0 | 0.9993 | −0.075 | 0.166 |
| 21.07 | C14:1 | 0.9990 | −0.027 | 0.080 |
| 21.87 | C15:0 | 0.9992 | −0.056 | 0.165 |
| 24.48 | C16:0 | 0.9986 | −0.145 | 0.165 |
| 25.69 | C16:1 | 0.9989 | −0.029 | 0.068 |
| 29.24 | C18:0 | 0.9978 | −0.130 | 0.139 |
| 29.95 | C18:1n9t | 0.9986 | −0.065 | 0.128 |
| 30.28 | C18:1n9c | 0.9986 | −0.065 | 0.064 |
| 32.06 | C18:2n6c | 0.9969 | −0.042 | 0.063 |
| 33.38 | C18:3n6 | 0.9970 | −0.032 | 0.048 |
| 34.29 | C18:3n3 | 0.9960 | −0.042 | 0.057 |
| 34.75 | C20:1 | 0.9920 | −0.044 | 0.057 |
| 36.18 | C21:0 | 0.9947 | −0.072 | 0.082 |
| 36.81 | C20:2 | 0.9941 | −0.044 | 0.050 |
| 38.27 | C20:3n6 | 0.9935 | −0.038 | 0.042 |
| 39.26 | C20:3n3 | 0.9843 | −0.068 | 0.060 |
| 39.36 | C20:4n6 | 0.9992 | −0.010 | 0.029 |
| 39.82 | C22:1n9 | 0.9942 | −0.031 | 0.035 |
| 42.03 | C20:5n3 | 0.9936 | −0.041 | 0.045 |
| 48.29 | C22:6n3 | 0.9888 | −0.025 | 0.023 |

Figure 9:
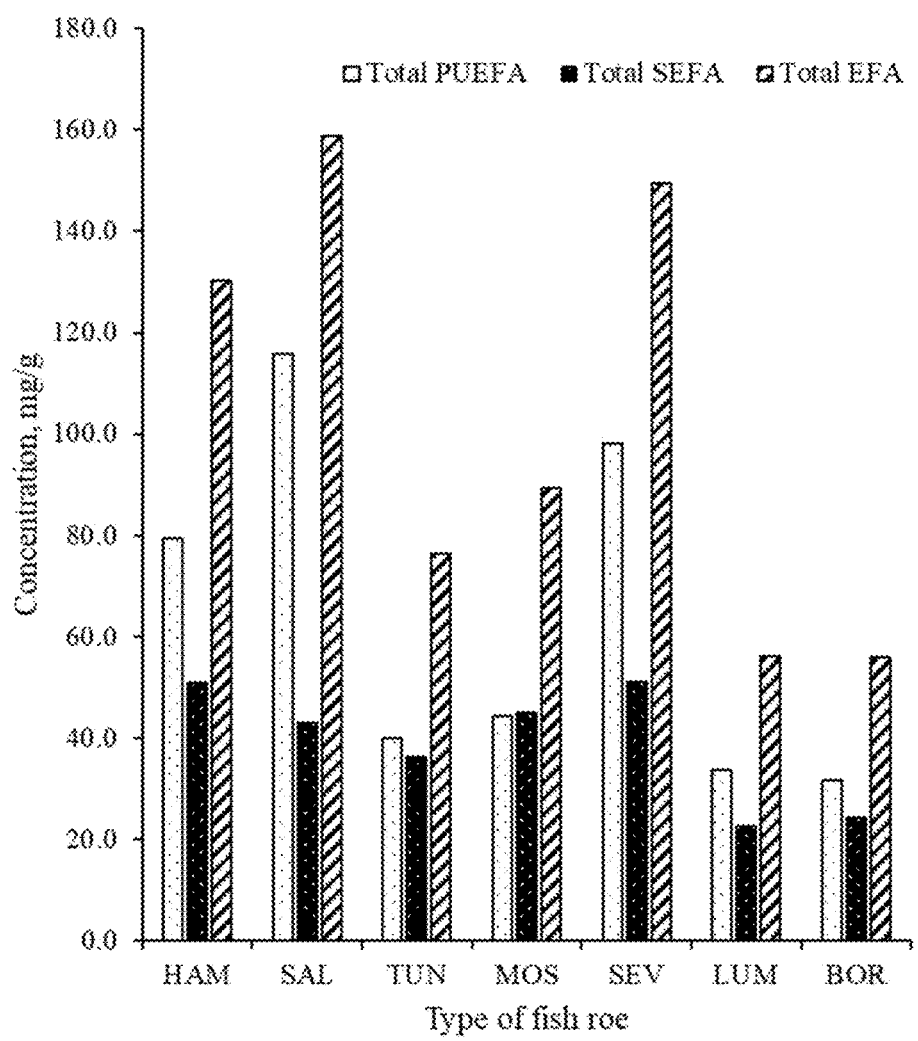
FIG. 9 shows total concentrations of PUEFA, SEFA, and EFA in lipid mass extracted from seven types of fish roe.
Figure 10:
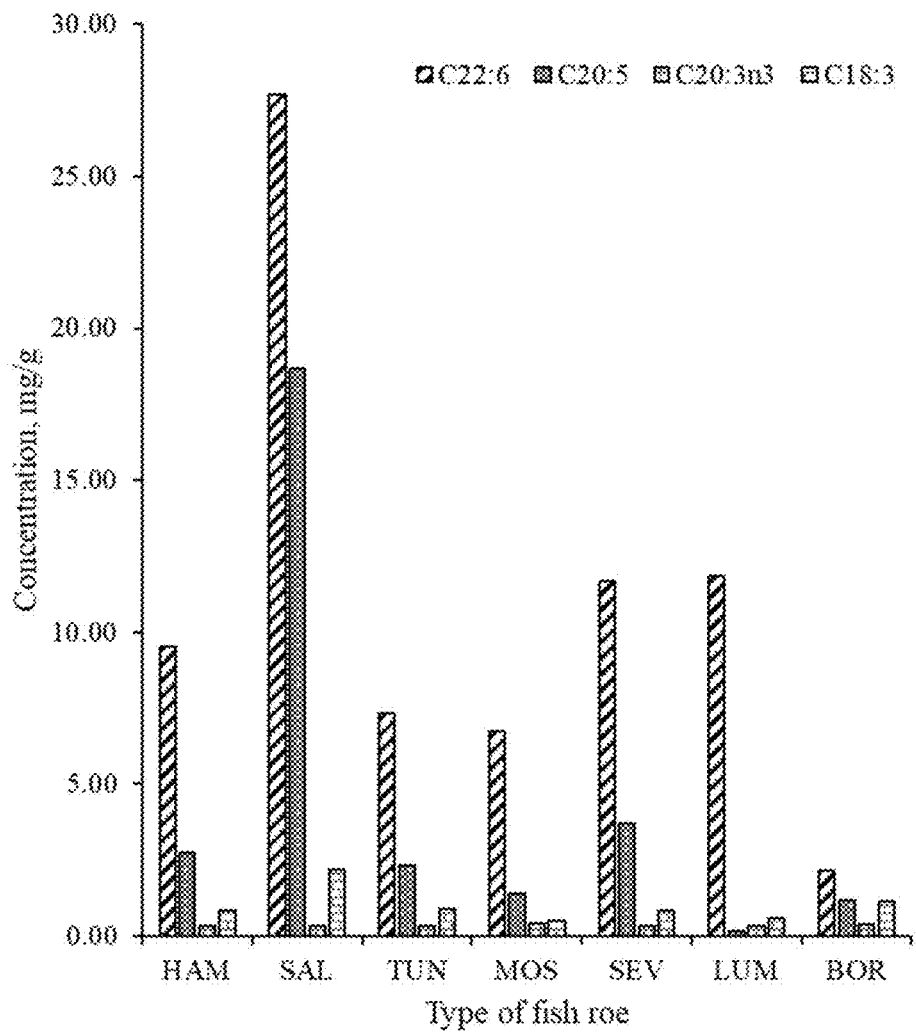
FIG. 10 shows concentrations of C22:6, C20:5, C20:3, and C18:3 in each type of investigated fish roe.

The EFA composition in seven types of FR-lipid extract was quantified, as shown in TABLE 10. The EFA content and PUEFA were maximum in SAL followed by SEV and HAM, as shown in FIG. 9. Salmon FR showed the highest DHA content, 27.69 mg/g, followed by lump FR, 11.85 mg/g. Generally, the total EFA composition was relatively highest in SAL followed by SEV and HAM. The ratio of Docosahexaenoic acid (DHA) to Eicosapentaenoic acid (EPA) was a characteristic profile for each species. Lump roe extract showed the highest relative ratio of DHA to EPA reached 75.3:1, w/w, as shown in TABLE 10. Absolutely the highest concentration of DHA and EPA was found in SAL roe extract.

TABLE 10

The concentration of EFA in seven species of fish roe extract, n = 6

| EFA | The concentration of EFA in lipid extract, mg/g[1] | | | | | | |
|---|---|---|---|---|---|---|---|
| | HAM | SAL | TUN | MOS | SEV | LUM | BOR |
| C12:0 | 0.21 | 0.44 | 0.20 | 0.21 | 0.19 | 0.18 | 0.20 |
| C14:0 | 5.82 | 10.65 | 2.52 | 2.85 | 4.31 | 1.74 | 2.42 |
| C14:1 | 0.43 | 0.34 | 0.10 | 0.10 | 0.10 | 0.08 | 0.17 |
| C15:0 | 0.85 | 0.93 | 0.68 | 0.93 | 0.63 | 0.43 | 0.76 |
| C16:0 | 33.53 | 21.93 | 24.60 | 28.75 | 38.48 | 15.63 | 17.04 |
| C16:1 | 13.22 | 9.76 | 4.35 | 3.71 | 6.89 | 1.53 | 6.99 |
| C18:3n6 | 0.41 | 2.07 | 0.44 | 0.26 | 0.41 | 0.29 | 0.57 |
| C18:0 | 10.34 | 8.94 | 8.17 | 12.09 | 7.49 | 4.39 | 3.70 |
| C18:1n9t | 0.67 | 0.10 | 0.11 | 0.18 | 0.10 | 0.11 | 1.37 |
| C18:1n9c | 24.46 | 37.38 | 12.19 | 10.49 | 46.06 | 13.72 | 12.85 |
| C18:2n6c | 1.23 | 2.22 | 0.67 | 0.68 | 3.72 | 0.68 | 1.21 |
| C18:3n3 | 0.41 | 0.12 | 0.44 | 0.26 | 0.41 | 0.29 | 0.56 |
| C20:1 | 0.43 | 1.64 | 0.45 | 0.49 | 0.41 | 0.56 | 0.18 |
| C21:0 | 0.18 | 0.17 | 0.18 | 0.19 | 0.17 | 0.17 | 0.18 |
| C20:2 | 0.16 | 0.76 | 0.16 | 0.25 | 0.38 | 0.26 | 0.28 |
| C20:3n6 | 0.16 | 0.16 | 0.16 | 0.25 | 0.15 | 0.15 | 0.20 |
| C20:3n3 | 0.19 | 0.19 | 0.20 | 0.19 | 0.19 | 0.20 | 0.19 |
| C20:4n6 | 25.05 | 14.07 | 10.92 | 19.12 | 23.54 | 3.26 | 3.54 |
| C22:1n9 | 0.25 | 0.60 | 0.19 | 0.19 | 0.30 | 0.51 | 0.23 |
| C20:5n3 | 2.76 | 18.69 | 2.32 | 1.39 | 3.72 | 0.16 | 1.19 |
| C22:6n3 | 9.52 | 27.69 | 7.34 | 6.75 | 11.69 | 11.85 | 2.15 |
| Total PUEFA[2] | 79.35 | 115.79 | 40.04 | 44.31 | 98.07 | 33.65 | 31.68 |
| Total SEFA[3] | 50.93 | 43.07 | 36.36 | 45.02 | 51.27 | 22.54 | 24.3 |
| Total EFA[4] | 130.28 | 158.86 | 76.39 | 89.33 | 149.34 | 56.19 | 55.98 |
| DHA %[5] | 7.31 | 17.43 | 9.61 | 7.56 | 7.83 | 21.09 | 3.84 |
| EPA %[5] | 2.12 | 11.77 | 3.04 | 1.56 | 2.49 | 0.28 | 2.13 |
| ALA %[5] | 0.63 | 1.38 | 1.15 | 0.58 | 0.55 | 1.03 | 2.02 |
| Ratio, DHA:EPA | 3.4 | 1.5 | 3.2 | 4.8 | 3.1 | 75.3 | 1.8 |

[1]The relative standard deviation of all determined concentrations was not more than 0.34%, for six determinations
[2]Poly-unsaturated esterified fatty acids
[3]Saturated esterified fatty acid
[4]Esterified fatty acids
[5]% of total fatty acids, g/g %

Figure 12:
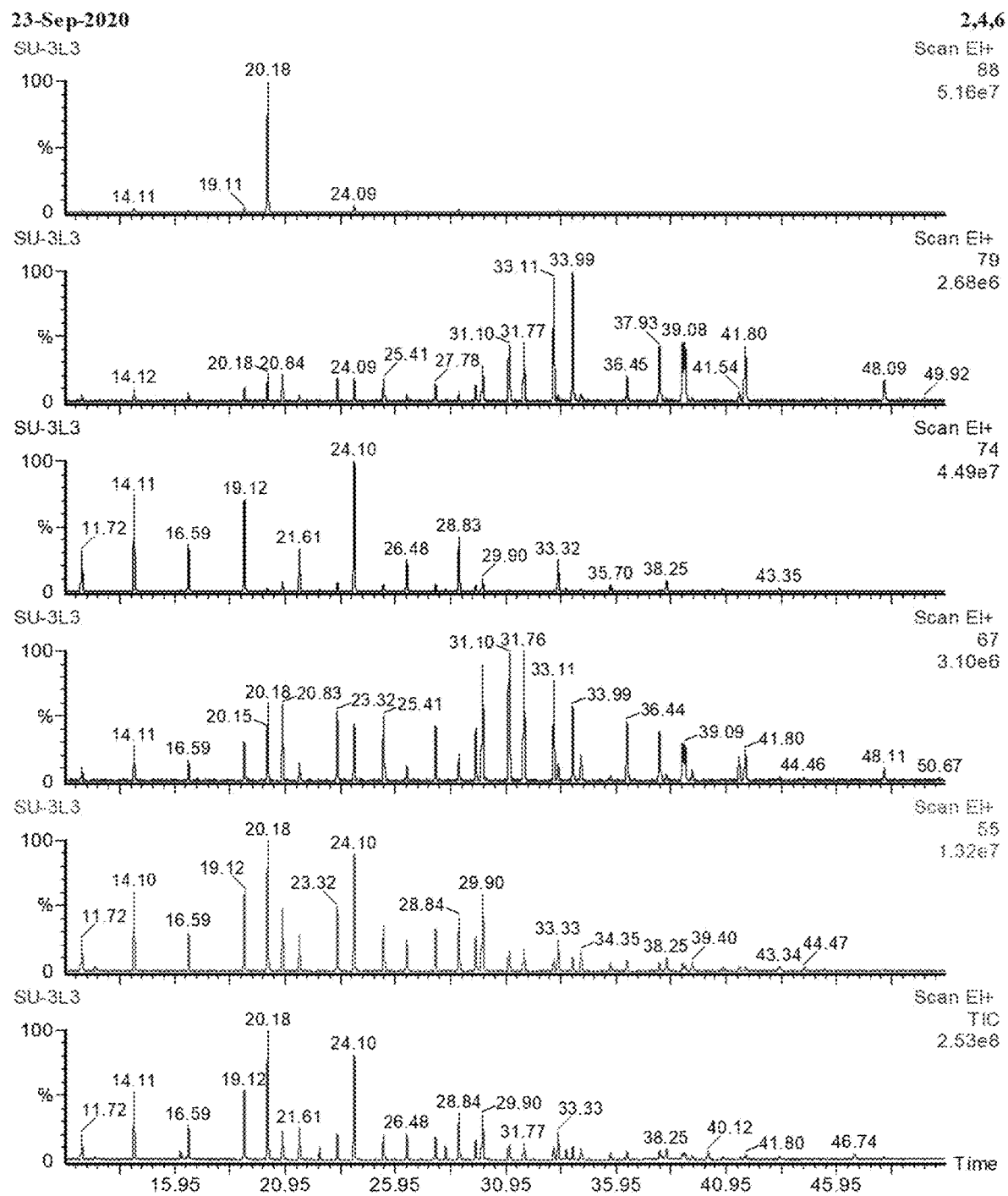
FIG. 12 shows representative TIC and extracted ion chromatograms at the most abundant m/z of the calibration solution.
Figure 13:
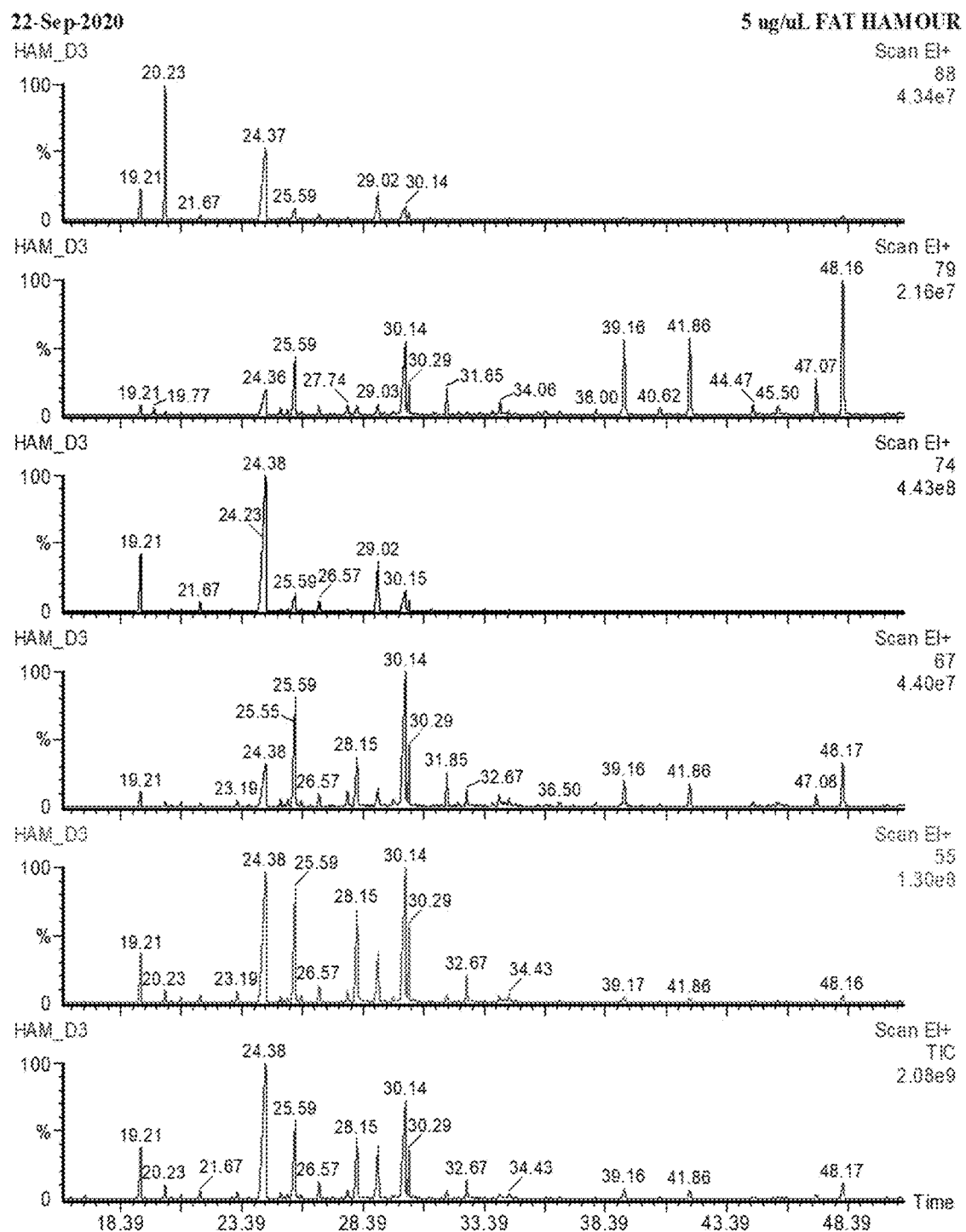
FIG. 13 shows representative TIC and extracted ion chromatograms at the most abundant m/z of hamour roe extract.

Compared with the other six species investigated. Bory FR showed, relatively, the lowest composition of DHA and EPA. The precision of lipid composition: The relative standard deviation of all determined concentrations was not more than 0.34%, for six determinations. Referring to FIG. 11A-B, the peak area integration of the two overlapped peaks corresponding to C20:3n3 and C20:4n6 is shown. The TerboMass-integration method was set to separate both overlapped peaks by extracting the matched EI-MS scan predefined at the corresponding elution time window. FIG. 12 shows a representative TIC and extracted ion chromatograms at the most abundant m/z (Table 4) of the FAME-calibration solution, lever 3. Further, FIG. 13 shows a representative TIC and extracted ion chromatograms at the most abundant m/z of Hamour roe extract.

Example 3

Characterization of Phospholipids

In order to characterize the extracted phospholipids, an ion-trap mass spectrometer was used. The ion-trap mass spectrometer was programmed to auto-fragmentation mode, $MS^n$, to characterize the detected PL. For more clear MS characterization, three steps of MS-fragmentation were applied to each precursor ion. Also, due to the co-elution of some minor and major PLs, a maximum number of auto-selected precursor ions was set to three. The sample was analyzed several times, applying different fragmentation thresholds and exclusion of some major identified PLs to enable fragmentation of minor intensity peaks. This interchangeable MS fragmentation method was applied for much clear characterization of minor PLs overlapped with major co-eluted PLs [24]. This approach enables linking the pathway of generated productions and the two base peak ions.

TABLE 11-12 show the most common LPCs, and PCs found and characterized fish roe extract. The fragmentation pathway of LPCs, PCs have been described in detail by Khedr et al. (2020) [24]. TABLE 12 is designed according to the MS-fragmentation pathway to facilitate the identification and verification of the structural composition of each PC through computational programming of the results of the mass spectrum scan for each compound. Once entering the values corresponding to the precursor ion, including $MS^2$ base peak (corresponds to $[M-FA1.CO_2H+H]+$, column A) and around 70% $MS^2$ ion fragment, corresponds to $[M-FA2.CO_2H+H]+$ (column B), are computed in the excel sheet, the remaining fragment ions, m/z value, which confirms the chemical structure of PC are auto-calculated [24].

TABLE 11

Fragmentation pattern of characterized LPCs in fish roe extract using IT-MS/MS

| FA, "m/z" | LPC | tR, min | [M + H]+ | $MS^2$ 100 | $MS^2$ >23% | $MS^3$ 100% $MS^3$ | $MS^3$ >30% | $MS^3$ >4% |
|---|---|---|---|---|---|---|---|---|
| 228 | 14:0 LPC | 21.79 | 468.4 | 450.4 | 184.0 | 391.2 | 255.2 | 267.2 |
| 240 | P_16:0 LPC[†] | 30.71 | 480.4 | 462.4 | 240.0 | 181.0 | 165.0 | 125.0 |
| 242 | 15:0 LPC | 24.87 | 482.4 | 464.4 | 184.0 | 405.4 | 269.4 | 281.4 |
| 242 | O_16:0 LPC[††] | 32.26 | 482.4 | 464.4 | 240.0 | 181.0 | 165.0 | 125.0 |
| 254 | 16:1 LPC | 23.58 | 494.4 | 476.4 | 184.0 | 417.4 | 281.4 | 293.4 |
| 256 | 16:0 LPC | 28.20 | 496.4 | 478.4 | 184.0 | 419.4 | 283.4 | 295.4 |
| 268 | 17:1 LPC | 26.11 | 508.4 | 490.4 | 240.0 | 181.0 | 165.0 | 125.0 |
| 268 | P_18:0 LPC[†] | 33.04 | 508.4 | 490.4 | 240.0 | 181.0 | 165.0 | 125.0 |
| 280 | 18:2 LPC | 25.43 | 520.4 | 502.4 | 184.0 | 443.2 | 307.2 | 319.2 |
| 282 | 18:1 LPC | 29.26 | 522.4 | 504.4 | 184.0 | 445.2 | 309.2 | 321.2 |
| 284 | 18:0 LPC | 34.51 | 524.4 | 506.4 | 184.0 | 447.2 | 311.2 | 323.2 |
| 302 | 20:5 LPC | 22.62 | 542.4 | 524.4 | 184.0 | 465.2 | 329.2 | 341.2 |
| 304 | 20:4 LPC | 25.51 | 544.4 | 526.4 | 184.0 | 467.2 | 331.2 | 343.2 |
| 306 | 20:3 LPC | 28.21 | 546.4 | 528.4 | 184.0 | 469.2 | 333.2 | 345.2 |
| 310 | 20:1 LPC | 35.67 | 550.4 | 532.4 | 184.0 | 473.2 | 337.2 | 349.2 |
| 328 | 22:6 LPC | 25.59 | 568.4 | 550.4 | 184.0 | 491.2 | 355.2 | 367.2 |
| 330 | 22:5 LPC iso1 | 27.51 | 570.4 | 552.4 | 184.0 | 493.2 | 357.2 | 369.2 |
| 330 | 22:5 LPC iso2 | 28.64 | 570.4 | 552.4 | 184.0 | 493.2 | 357.2 | 369.2 |

[†]Plasmenyl LPC
[††]Plasmanyl LPC

TABLE 12

Abundant $MS^2$ fragment ions of major PCs and auto-calculated $MS^2$ and $MS^3$ characteristic fragmentation ion products.

| FA1, m/z | FA2, m/z | PC name | $t_R$, min | [M + H]+ m/z[†] | $MS^2$ Fragment ions, m/z | | | | | | $MS^2$ (100%) to $MS^3$, m/z | | |
|---|---|---|---|---|---|---|---|---|---|---|---|---|---|
| | | | | | C | D | 100%, A[†] | ≈70%, B[†] | E | F | 100%, G | H | I |
| 256 | 228 | 16:0_14:0 PC | 57.62 | 706.5 | 647.5 | 523.2 | 450.2 | 478.2 | 468.2 | 496.2 | 391.2 | 419.2 | 256 |
| 254 | 254 | 16:1_16:1 PC | 54.34 | 730.5 | 671.5 | 547.2 | 476.2 | 476.2 | 494.2 | 494.2 | 417.2 | 41.27 | 282 |
| 228 | 280 | 14:0_18:2 PC | 57.67 | 730.5 | 671.5 | 547.2 | 502.2 | 450.2 | 520.2 | 468.2 | 443.2 | 391.2 | 308 |
| 256 | 254 | 16:0_16:1 PC | 58.81 | 732.5 | 673.5 | 549.2 | 476.2 | 478.2 | 494.2 | 496.2 | 417.2 | 419.2 | 282 |
| 256 | 256 | 16:0_16:0 PC | 63.80 | 734.5 | 675.5 | 551.2 | 478.2 | 478.2 | 496.2 | 496.2 | 419.2 | 419.2 | 284 |
| 242 | 280 | 15:0_18:2 PC | 58.49 | 744.5 | 685.5 | 561.2 | 502.2 | 464.2 | 520.2 | 482.2 | 443.2 | 405.2 | 308 |
| 268 | 256 | P-18:0_16:0 PC | 63.19 | 746.5 | 687.5 | 563.2 | 478.2 | 490.2 | 496.5 | 508.2 | 419.2 | 431.2 | 284 |
| 228 | 302 | 14:0_20:5 PC | 52.04 | 752.6 | 693.6 | 569.6 | 524.6 | 450.6 | 542.6 | 468.6 | 465.6 | 391.6 | 330 |
| 254 | 276 | 16:1_18:4 PC | 54.51 | 752.6 | 693.6 | 569.6 | 498.6 | 476.6 | 516.6 | 494.6 | 439.6 | 417.6 | 304 |
| 256 | 276 | 16:0_18:4 PC | 58.81 | 754.5 | 695.5 | 571.2 | 498.2 | 478.2 | 516.2 | 496.2 | 439.2 | 419.2 | 304 |
| 254 | 280 | 16:1_18:2 PC | 57.32 | 756.5 | 697.5 | 573.2 | 502.2 | 476.2 | 520.2 | 494.2 | 443.2 | 417.2 | 308 |

TABLE 12-continued

Abundant MS² fragment ions of major PCs and auto-calculated MS² and MS³ characteristic fragmentation ion products.

| FA1, m/z | FA2, m/z | PC name | $t_R$, min | [M + H]⁺ m/z† | MS² Fragment ions, m/z | | | | | | MS² (100%) to MS³, m/z | | |
|---|---|---|---|---|---|---|---|---|---|---|---|---|---|
| | | | | | C | D | 100%, A† | ≈70%, B† | E | F | 100%, G | H | I |
| 256 | 278 | 16:0_18:3 PC | 58.32 | 756.5 | 697.5 | 57.32 | 500.2 | 478.2 | 518.2 | 496.2 | 441.2 | 419.2 | 306 |
| 254 | 282 | 16:1_18:1 PC | 61.18 | 758.5 | 699.5 | 575.2 | 504.2 | 476.2 | 522.2 | 494.2 | 445.2 | 417.2 | 310 |
| 256 | 280 | 16:0_18:2 PC | 62.06 | 758.5 | 699.5 | 575.2 | 502.2 | 478.2 | 520.2 | 496.2 | 443.2 | 419.2 | 308 |
| 256 | 282 | 16:0_18:1 PC | 65.78 | 760.5 | 701.5 | 577.2 | 504.2 | 478.2 | 522.2 | 496.2 | 445.2 | 419.2 | 310 |
| 284 | 256 | 18:0_16:0 PC | 71.31 | 762.5 | 703.5 | 579.2 | 478.2 | 506.2 | 496.2 | 524.2 | 419.2 | 447.2 | 284 |
| 242 | 284 | 15:0_20:5 PC | 53.89 | 766.5 | 707.5 | 583.2 | 524.2 | 482.2 | 542.2 | 500.2 | 465.2 | 423.2 | 330 |
| 240 | 304 | 15:1_20:4 PC | 54.88 | 766.5 | 707.5 | 583.2 | 526.2 | 462.2 | 544.2 | 480.2 | 467.2 | 403.2 | 332 |
| 242 | 304 | 15:0_20:4 PC | 64.56 | 768.5 | 709.5 | 585.2 | 526.2 | 464.2 | 544.2 | 482.2 | 467.2 | 405.2 | 332 |
| 324 | 228 | P22:0_14:0 PC | 68.19 | 774.5 | 715.5 | 592.1 | 450.2 | 546.2 | 468.2 | 564.2 | 391.2 | 487.2 | 256 |
| 270 | 282 | 17:0_18:1 PC | 69.20 | 774.5 | 715.5 | 591.2 | 504.2 | 492.2 | 522.2 | 510.2 | 445.2 | 433.2 | 310 |
| 254 | 302 | 16:1_20:5 PC | 53.23 | 778.5 | 719.5 | 595.2 | 524.2 | 476.2 | 542.2 | 494.2 | 465.2 | 417.2 | 330 |
| 328 | 228 | 22:6_14:0 PC | 54.70 | 778.5 | 719.5 | 595.2 | 450.2 | 550.2 | 468.2 | 568.2 | 391.2 | 491.2 | 256 |
| 228 | 330 | 14:0_22:5 PC | 56.66 | 780.5 | 721.5 | 597.2 | 552.2 | 450.2 | 570.2 | 468.2 | 493.2 | 391.2 | 358 |
| 256 | 302 | 16:0_20:5 PC | 57.82 | 780.8 | 721.5 | 597.2 | 524.2 | 478.2 | 542.2 | 496.2 | 465.2 | 419.2 | 330 |
| 228 | 332 | 14:0_22:4 PC | 59.74 | 782.5 | 723.5 | 599.2 | 554.6 | 450.6 | 571.6 | 468.6 | 495.6 | 391.6 | 360 |
| 256 | 304 | 16:0_20:4 PC | 61.08 | 782.5 | 723.5 | 599.2 | 526.2 | 478.2 | 544.2 | 496.2 | 467.2 | 419.2 | 332 |
| 278 | 282 | 18:3_18:1 PC | 65.84 | 782.5 | 723.5 | 599.2 | 504.2 | 500.2 | 522.2 | 518.2 | 445.2 | 441.2 | 310 |
| 282 | 280 | 18:1_18:2 PC | 63.34 | 784.5 | 725.5 | 601.2 | 502.2 | 504.2 | 520.2 | 522.2 | 443.2 | 445.2 | 308 |
| 256 | 306 | 16:0_20:3 PC | 63.95 | 784.5 | 725.5 | 601.2 | 528.2 | 478.2 | 546.2 | 496.2 | 469.2 | 419.2 | 334 |
| 284 | 278 | 18:0_18:3 PC | 65.81 | 784.5 | 725.5 | 601.2 | 500.2 | 506.2 | 518.2 | 524.2 | 441.2 | 447.2 | 306 |
| 256 | 308 | 16:0_20:2 PC | 67.01 | 786.5 | 727.5 | 603.2 | 530.2 | 478.6 | 548.2 | 496.6 | 471.2 | 419.6 | 336 |
| 282 | 282 | 18:1_18:1 PC | 68.13 | 786.5 | 727.5 | 603.2 | 504.2 | 504.2 | 522.2 | 522.2 | 445.2 | 445.2 | 310 |
| 284 | 280 | 18:0_18:2 PC | 69.76 | 786.5 | 727.5 | 603.2 | 502.2 | 506.2 | 520.2 | 524.2 | 443.2 | 447.2 | 308 |
| 284 | 280 | 18:0_18:1 PC | 71.80 | 788.5 | 729.5 | 605.2 | 504.2 | 506.2 | 522.2 | 524.2 | 445.2 | 447.2 | 310 |
| 242 | 328 | 15:0_22:6 PC | 57.54 | 792.5 | 733.4 | 609.2 | 550.2 | 464.2 | 568.2 | 482.2 | 491.2 | 405.2 | 356 |
| 242 | 328 | P16:0_22:6 PC | 64.32 | 792.5 | 733.5 | 609.2 | 550.2 | 464.2 | 568.2 | 482.2 | 491.2 | 405.2 | 356 |
| 270 | 304 | 17:0_20:4 PC | 64.30 | 796.5 | 737.5 | 613.2 | 526.2 | 492.2 | 544.2 | 510.2 | 467.2 | 433.2 | 332 |
| 254 | 328 | 16:1_22:6 PC | 55.96 | 804.6 | 745.6 | 621.6 | 550.6 | 476.6 | 568.6 | 494.6 | 491.6 | 417.6 | 356 |
| 282 | 302 | 18:1_20:5 PC | 58.16 | 806.6 | 747.6 | 623.6 | 524.6 | 504.6 | 542.6 | 522.6 | 465.6 | 445.6 | 330 |
| 256 | 328 | 16:0_22:6 PC | 59.59 | 806.6 | 747.6 | 623.6 | 550.6 | 478.6 | 568.6 | 496.6 | 491.6 | 419.6 | 356 |
| 282 | 304 | 18:1_20:4 PC | 59.47 | 808.6 | 749.6 | 625.6 | 526.6 | 504.6 | 544.6 | 522.6 | 467.6 | 445.6 | 332 |
| 256 | 330 | 16:0_22:5 PC | 61.62 | 808.6 | 749.6 | 625.6 | 552.6 | 478.6 | 570.6 | 496.6 | 493.6 | 419.6 | 358 |
| 284 | 302 | 18:0_20:5 PC | 62.69 | 808.6 | 749.6 | 625.6 | 524.2 | 506.2 | 542.2 | 524.2 | 465.2 | 447.2 | 330 |
| 282 | 306 | 18:1_20:3 PC | 65.72 | 810.6 | 751.6 | 627.6 | 528.6 | 504.6 | 546.6 | 522.6 | 469.6 | 445.6 | 334 |
| 256 | 332 | 16:0_22:4 PC | 67.21 | 810.6 | 751.6 | 627.6 | 554.6 | 478.6 | 572.6 | 496.6 | 495.6 | 419.6 | 360 |
| 284 | 304 | 18:0_20:4 PC | 71.72 | 810.6 | 751.6 | 627.6 | 526.6 | 506.6 | 544.6 | 524.6 | 467.6 | 447.6 | 332 |
| 282 | 304 | 18:1_20:2 PC | 68.98 | 812.6 | 753.6 | 629.6 | 530.6 | 508.6 | 548.6 | 526.6 | 471.6 | 449.6 | 336 |
| 284 | 306 | 18:0_20:3 PC | 69.88 | 812.6 | 753.6 | 629.6 | 528.6 | 506.6 | 546.6 | 524.6 | 469.6 | 447.6 | 334 |
| 280 | 302 | 18:2_20:1 PC | 71.58 | 812.6 | 753.6 | 629.6 | 532.6 | 510.6 | 550.6 | 528.6 | 473.6 | 451.6 | 338 |
| 282 | 310 | 18:1_20:1 PC | 72.61 | 814.6 | 755.6 | 631.6 | 532.2 | 504.2 | 550.2 | 522.2 | 473.2 | 445.2 | 338 |
| 268 | 328 | P-18:0_22:6 PC | 58.87 | 818.6 | 759.6 | 635.6 | 550.6 | 490.6 | 568.6 | 508.6 | 491.6 | 431.6 | 356 |
| 284 | 312 | 18:0_20:0 PC | 65.16 | 818.6 | 759.6 | 635.6 | 534.6 | 506.6 | 552.6 | 524.6 | 475.6 | 447.6 | 340 |
| 328 | 270 | 22:6_17:0 PC | 62.63 | 820.6 | 761.6 | 637.6 | 492.6 | 550.6 | 511.6 | 568.6 | 433.6 | 491.6 | 298 |
| 270 | 328 | 17:0_22:6 PC | 63.54 | 820.6 | 761.6 | 637.6 | 550.6 | 492.6 | 568.6 | 510.6 | 491.6 | 433.6 | 356 |
| 328 | 278 | 22:6_18:3 PC | 58.94 | 828.6 | 769.6 | 645.6 | 500.6 | 550.6 | 518.6 | 568.6 | 441.6 | 491.6 | 306 |
| 278 | 328 | 18:3_22:6 PC | 60.31 | 828.6 | 769.6 | 645.6 | 550.6 | 500.6 | 568.6 | 518.6 | 491.6 | 441.6 | 356 |
| 304 | 304 | 20:4_20:4 PC | 62.50 | 830.6 | 771.6 | 647.6 | 526.6 | 526.6 | 544.6 | 544.6 | 467.6 | 467.6 | 332 |
| 326 | 282 | 21:0_18:1 PC | 63.86 | 830.6 | 771.6 | 647.6 | 504.6 | 548.6 | 522.6 | 566.6 | 445.6 | 489.6 | 310 |
| 326 | 284 | 21:0_18:0 PC | 60.75 | 832.6 | 773.6 | 649.6 | 506.6 | 548.6 | 524.6 | 566.6 | 447.6 | 489.6 | 312 |
| 282 | 330 | 18:1_22:5 PC | 63.63 | 834.6 | 775.6 | 651.6 | 552.6 | 504.6 | 570.6 | 522.6 | 493.6 | 445.6 | 358 |
| 280 | 332 | 18:2_22:4 PC | 65.08 | 834.6 | 775.6 | 651.6 | 554.6 | 502.6 | 572.6 | 520.6 | 495.6 | 443.6 | 360 |
| 284 | 328 | 18:0_22:6 PC | 66.87 | 834.6 | 775.6 | 651.6 | 550.6 | 506.6 | 568.6 | 524.6 | 491.6 | 447.6 | 356 |
| 284 | 330 | 18:0_22:5 PC | 68.56 | 836.6 | 777.6 | 653.6 | 552.6 | 506.6 | 570.6 | 524.6 | 493.6 | 447.6 | 358 |
| 282 | 332 | 18:1_22:4 PC | 69.78 | 836.6 | 777.6 | 653.6 | 554.6 | 504.6 | 572.6 | 522.6 | 495.6 | 445.6 | 360 |
| 314 | 332 | 18:0_22:4 PC | 71.54 | 838.6 | 77.96 | 655.6 | 524.6 | 506.6 | 542.6 | 524.6 | 465.6 | 447.6 | 330 |

†Computed m/z value as obtained from the MS" spectrum.
FA1: Fatty acid acyl at sn-1; FA2: Fatty acid acyl at sn-2; PC: Phosphatidylcholine.
FA1 = 'precursor ion - column A',
FA2 = 'precursor ion - column B',
column C = 'precursor ion - 59',
column D = 'precursor ion - 183',
column E = 'precursor ion - FA1 +2',
column F = 'precursor ion - FA2 +2',
column G = 'value in column A - 59',
column H = 'value in column B - 59',
column I = 'precursor ion - FA1 - 194'

Figure 14:
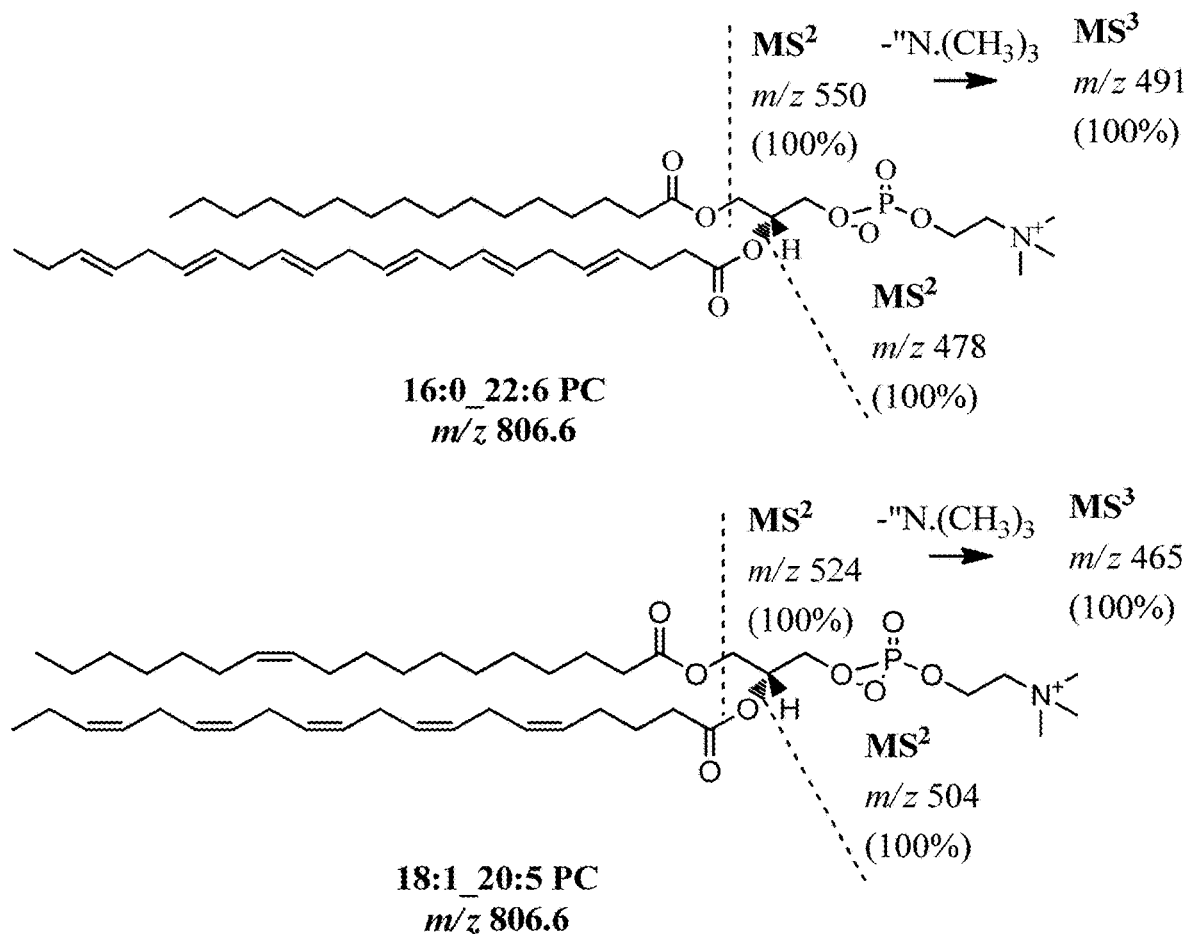
FIG. 14 shows a schematic MS fragmentation pathway of 16:0_22:6 PC and 18:1_20:5 PC, both m/z 806.6.

FIG. 14 shows a representative fragmentation pathway of two PCs, m/z 806.6, showing the cleavage priorities. For fast and ease of searching for LPCs, and positive ion of m/z 184 was extracted, and the neutral loss ions of m/z 59 and 183 were extracted for the allocation of PCs. Sixty-six PCs and eighteen LPCs were characterized at definite retention time ($t_R$). The productions and abundance of LPEs and PEs were computed in an excel sheet format for fast and accurate identification of the detected analyte, as shown in TABLE 13-14. The PEs were allocated in the IT-MS scan chromatogram by extracting the m/z 141, which corresponds to the neutral loss of dimethyl-ethanolamine moiety "—O—$CH_2$—$CH_2$—$N(CH_3)_2$". Sixteen LPEs and 29 PEs were identified and confirmed in the fish roe extract.

TABLE 13

Fragmentation pattern of characterized LPEs in fish roe extract using IT-MS.

| FA, "m/z" | LPE | $t_R$, min | [M + H]⁺ | $MS^2$ 100 | $MS^2$ >23% | $MS^3$ 100% $MS^3$ | $MS^3$ >30% |
|---|---|---|---|---|---|---|---|
| 228 | 14:0 LPE | 12.80 | 426.4 | 408.4 | 285 | 363 | 381 |
| 242 | 15:0 LPE | 23.21 | 440.4 | 422.4 | 299 | 377 | 395 |
| 254 | 16:1 LPE | 17.25 | 452.4 | 434.4 | 311 | 389 | 407 |
| 256 | 16:0 LPE | 14.13 | 454.4 | 436.4 | 313 | 391 | 409 |
| 270 | 17:0 LPE | 13.20 | 468.4 | 450.4 | 327 | 405 | 423 |
| 270 | O-18:0 LPE | 19.76 | 468.4 | 450.4 | 327 | 405 | 423 |
| 276 | 18:4 LPE | 14.24 | 474.4 | 456.4 | 333 | 411 | 429 |
| 278 | 18:3 LPE | 14.23 | 476.4 | 458.4 | 335 | 413 | 431 |
| 280 | 18:2 LPE | 27.45 | 478.4 | 460.4 | 337 | 415 | 433 |
| 282 | 18:1 LPE | 28.01 | 480.4 | 462.4 | 339 | 417 | 435 |
| 284 | 18:0 LPE | 16.64 | 482.4 | 464.4 | 341 | 419 | 437 |
| 302 | 20:5 LPE | 13.08 | 500.4 | 482.4 | 359 | 437 | 455 |
| 306 | 20:3 LPE | 17.05 | 504.4 | 486.4 | 363 | 441 | 459 |
| 310 | 20:1 LPE | 26.25 | 508.4 | 490.4 | 367 | 445 | 463 |
| 328 | 22:6 LPE | 13.87 | 526.4 | 508.4 | 385 | 463 | 481 |
| 330 | 22:5 LPE | 23.97 | 528.4 | 510.4 | 387 | 465 | 483 |

TABLE 14

Abundant $MS^2$ fragment ions of major PEs and auto-calculated product ions.

| FA1, m/z | FA2, m/z | PE | $t_R$, min | [M + H]⁺ | C | D | A | B | E | F | G | H | I | J |
|---|---|---|---|---|---|---|---|---|---|---|---|---|---|---|
| 256 | 280 | 16:0_18:2 PE | 37.94 | 716.5 | 672 | 575 | 460 | 436 | 442 | 417 | 418 | 393 | 239 | 263 |
| 256 | 282 | 16:0_18:1 PE | 40.77 | 718.5 | 674 | 577 | 462 | 436 | 444 | 419 | 418 | 393 | 239 | 265 |
| 240 | 304 | P16:0_20:4 PE | 18.12 | 724.5 | 680 | 583 | 484 | 420 | 466 | 441 | 402 | 377 | 223 | 287 |
| 256 | 302 | 16:0_20:5 PE | 36.17 | 738.5 | 694 | 597 | 482 | 436 | 464 | 439 | 418 | 393 | 239 | 285 |
| 256 | 304 | 16:0_20:4 PE | 38.28 | 740.5 | 696 | 599 | 484 | 436 | 466 | 441 | 418 | 393 | 239 | 287 |
| 240 | 332 | P15:1_22:6 PE | 39.49 | 748.5 | 704 | 607 | 508 | 416 | 490 | 465 | 398 | 373 | 223 | 315 |
| 240 | 330 | P16:0_22:5 PE | 39.48 | 750.5 | 706 | 609 | 510 | 420 | 492 | 467 | 402 | 377 | 223 | 313 |
| 268 | 302 | P18:0_20:5 PE | 40.68 | 750.5 | 706 | 609 | 482 | 448 | 464 | 439 | 430 | 405 | 251 | 285 |
| 268 | 304 | P18:0_20:4 PE | 37.68 | 752.5 | 708 | 611 | 484 | 448 | 466 | 441 | 430 | 405 | 251 | 287 |
| 240 | 332 | P16:0_22:4 PE | 39.89 | 752.5 | 708 | 611 | 515 | 420 | 494 | 469 | 402 | 377 | 223 | 315 |
| 256 | 328 | 16:0_22:6 PE | 38.24 | 764.5 | 720 | 623 | 508 | 436 | 490 | 465 | 418 | 393 | 239 | 311 |
| 282 | 304 | 18:1_20:4 PE | 39.30 | 766.5 | 722 | 625 | 484 | 462 | 466 | 441 | 444 | 419 | 265 | 287 |
| 284 | 302 | 18:0_20:5 PE | 40.26 | 766.5 | 722 | 625 | 482 | 464 | 464 | 439 | 446 | 421 | 267 | 285 |
| 284 | 304 | 18:0_20:4 PE iso | 41.07 | 768.5 | 724 | 627 | 484 | 464 | 466 | 441 | 446 | 421 | 267 | 287 |
| 284 | 304 | 18:0_20:4 PE | 42.25 | 768.5 | 724 | 627 | 484 | 464 | 466 | 441 | 446 | 421 | 267 | 287 |
| 256 | 338 | 16:0_22:1 PE | 46.94 | 774.5 | 730 | 633 | 518 | 436 | 500 | 475 | 418 | 393 | 239 | 321 |
| 314 | 284 | P22:5_18:0 PE | 48.67 | 776.5 | 732 | 635 | 462 | 492 | 444 | 419 | 474 | 449 | 297 | 267 |
| 270 | 328 | O-18:0_22:6 PE | 44.19 | 778.5 | 734 | 637 | 508 | 450 | 490 | 465 | 432 | 407 | 253 | 311 |
| 278 | 328 | 18:3_22:6 PE | 38.20 | 786.5 | 742 | 645 | 508 | 458 | 490 | 465 | 440 | 415 | 261 | 311 |
| 282 | 328 | 18:1_22:6 PE | 39.16 | 790.5 | 746 | 649 | 508 | 462 | 490 | 465 | 444 | 419 | 265 | 311 |
| 280 | 332 | 18:2_22:4 PE | 41.57 | 792.5 | 748 | 651 | 512 | 460 | 494 | 469 | 442 | 417 | 263 | 315 |
| 328 | 284 | 22:6_18:0 PE | 42.25 | 792.5 | 748 | 651 | 464 | 508 | 446 | 421 | 490 | 465 | 311 | 267 |
| 284 | 328 | 18:0_22:6 PE | 43.21 | 792.5 | 748 | 651 | 508 | 464 | 490 | 465 | 446 | 421 | 267 | 311 |
| 330 | 284 | 22:5_18:0 PE | 43.06 | 794.5 | 750 | 653 | 464 | 510 | 446 | 421 | 492 | 467 | 313 | 267 |
| 284 | 330 | 18:0_22:5 PE | 43.68 | 794.5 | 750 | 653 | 510 | 464 | 492 | 467 | 446 | 421 | 267 | 313 |
| 284 | 332 | 18:0_22:4 PE | 46.20 | 796.5 | 752 | 655 | 512 | 464 | 494 | 469 | 446 | 421 | 267 | 315 |
| 256 | 330 | 18:0_22:5 PE | 48.73 | 808.5 | 764 | 667 | 552 | 478 | 534 | 509 | 460 | 435 | 239 | 313 |
| 284 | 302 | 18:0_22:4 PE | 50.07 | 808.5 | 764 | 667 | 524 | 506 | 506 | 481 | 488 | 463 | 267 | 285 |
| 306 | 328 | 20:3_22:6 PE | 44.85 | 814.5 | 770 | 673 | 508 | 486 | 490 | 465 | 468 | 443 | 289 | 311 |

C, [M + H]-44
D, [M + H]-141
E, column A-18
F, column A-43
G, column B-18
H, column B-43
I, column FA1-17
J, column FA2-17

The extracted phospholipids are quantified by the analysis method as described herein. A standard solution mixture containing three internal standards were prepared in solvent 1 and mixed in a constant concentration of 10 ng/μL with calibrant solution mixture containing C1; 19:0_LPC (m/z 538.4), C2; 17:0_17:0 PC (m/z 762.6) and C3; 17:0_17:0 PE (m/z 720.5) at concentration spanning the range of 0.5 to 150 ng/μL. The calibration curve of each PLs representative group was constructed by plotting the peak area ratio of C1(m/z 538.4) to IS1(m/z 510.3) "Curve 1", C2(m/z 762.6) to IS2(m/z 818.6) "Curve 2", and C3(m/z 720.5) to IS3(m/z 664.5) "Curve 3" versus the concentration as ng/μL. The retention time of IS1, IS2, IS3, C1, C2, and C3 was 30.7, 72.7, 43.9, 37.4, 60.0, 46.9 min, respectively. The response factors, forced to zero for curves 1, 2, and 3 were 0.1433, 0.3143, and 0.0704 for LPCs, PCs, and Pes & LPEs. Dilution was necessary for some samples that showed concentration levels exceed 100 ng/μL. The validity of the quantitative analysis method was checked as per our previous article [24, 25]. The total ion chromatograms obtained from the LC-QqQ-MS were. The corresponding precursor ions of each PL were extracted from the total ion chromatogram obtained from LC-QqQ-MS analysis. The peak area of each extracted precursor ion was integrated and divided by the IS peak area, and the concentration was calculated from the corresponding calibration curve.

Figure 15:
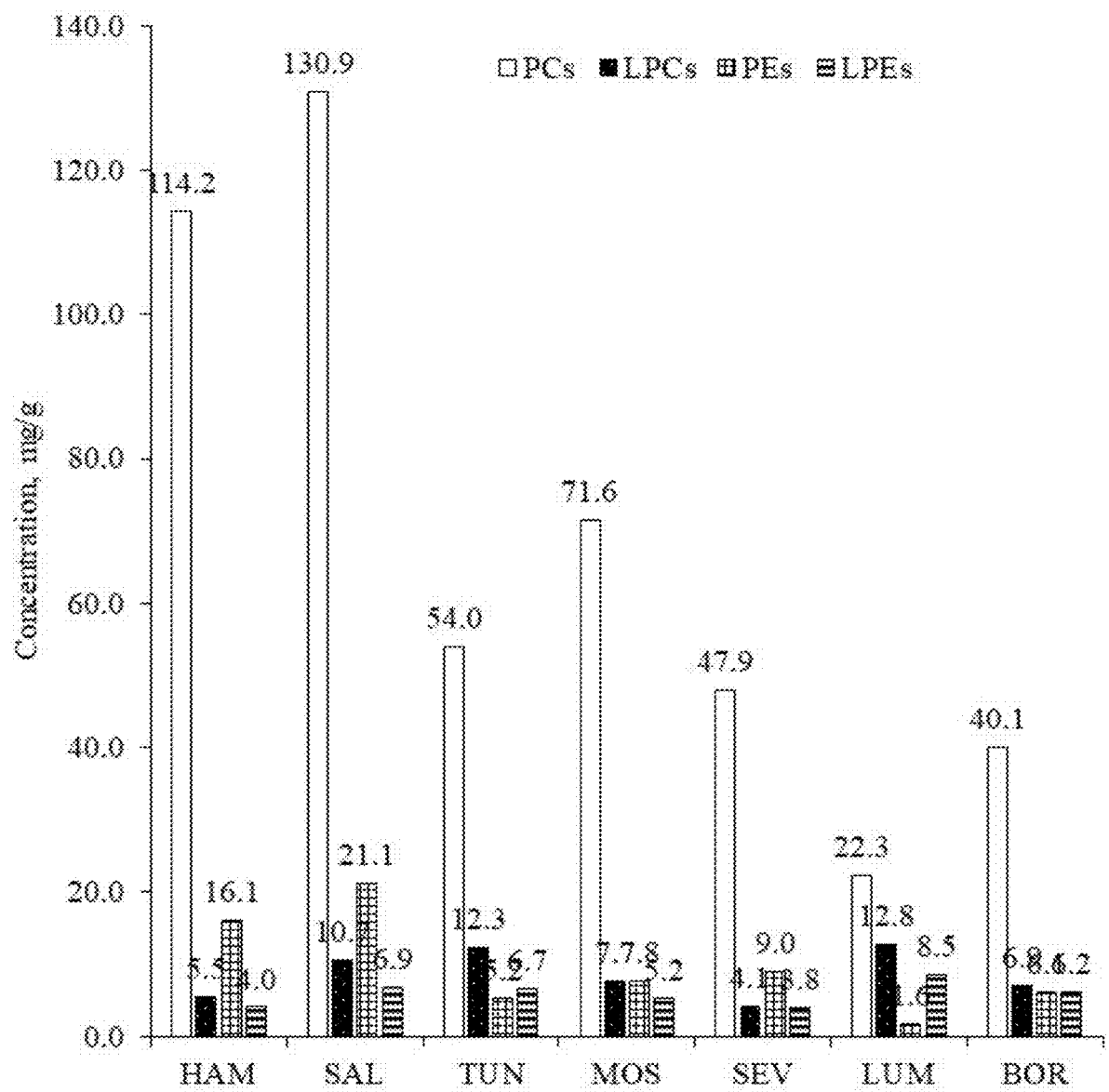
FIG. 15 shows concentrations of PCs, LPCs, PEs, and LPEs in each type of the roe-extract.
Figure 16:
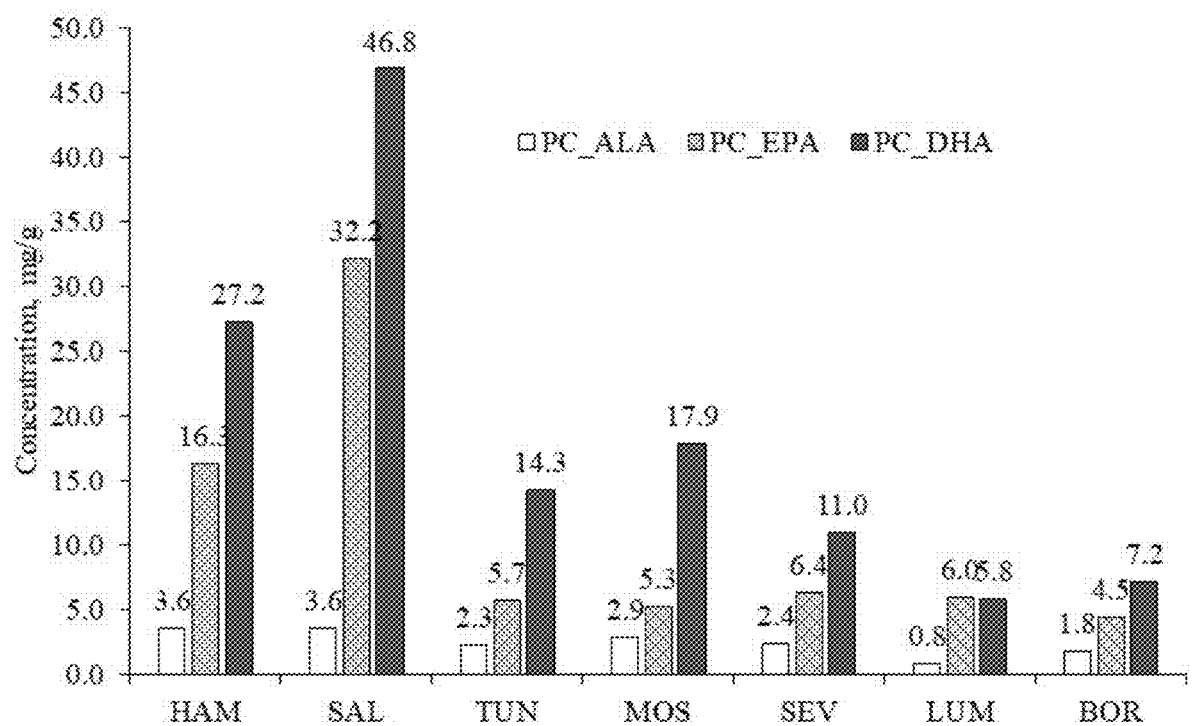
FIG. 16 shows concentrations of PCs containing esterified ALA, EPA, and DHA.

Referring to TABLE 15-18, the concentrations of LPCs, PCs, LPEs, and PEs were shown. The total amount of investigated PLs was calculated in each type of roe extract. Salmon and hamour roe extracts were the richest types in PCs and PEs (FIG. 15). TABLE 15 shows SAL roe extract contains the highest concentration of 22:6_LPC compared with other roe species, 2.62 mg/g. Also, a relatively high concentration of 20:5_LPC was found in LUM and SAL, equal to 2.05, 1.98 mg/g, respectively. However, C18: 3_LPC has existed at deficient concentration, 0.01 to 0.02 mg/g, in all roe extracts (TABLE 15). Each FR dried powder sample was extracted and quantified five times to calculate the concentration precision for every single phospholipid. The relative standard deviation of all assayed compounds was within a range of 1.05 to 5.70%. The total concentration of PCs containing esterified C22:6 (DHA) and C20:5 (EPA) was relatively high in SAL (46.8, 32.2, respectively), followed by HAM (27.2, 16.3, respectively), as shown in FIG. 16 and TABLE 16. All FR extracts showed a relatively greater total concentration of PCs than LPCs.

TABLE 15

The concentration of LPCs in seven species of fish roe extracts

| | | | Concentration, mg/g | | | | | | |
|---|---|---|---|---|---|---|---|---|---|
| PC | $t_R$, min | $[M + H]^+$ | HAM | SAL | TUN | MOS | SEV | LUM | BOR |
| 14:0 LPC | 21.79 | 468.4 | 0.11 | 0.49 | 0.28 | 0.15 | 0.02 | 0.29 | 0.10 |
| P_16:0 LPC | 30.71 | 480.4 | 0.03 | 0.01 | 0.00 | 0.05 | 0.00 | 0.00 | 0.00 |
| 15:0 LPC | 24.87 | 482.4 | 0.02 | 0.04 | 0.15 | 0.05 | 0.01 | 0.07 | 0.06 |
| O_16:0 LPC | 32.26 | 482.4 | 0.13 | 0.02 | 0.11 | 0.26 | 0.06 | 0.37 | 0.23 |
| 16:1 LPC | 23.58 | 494.4 | 0.18 | 0.16 | 0.52 | 0.21 | 0.05 | 0.14 | 0.23 |
| 16:0 LPC | 28.20 | 496.4 | 2.15 | 2.66 | 4.59 | 3.89 | 1.77 | 3.93 | 3.28 |
| 17:1 LPC | 26.11 | 508.4 | 0.06 | 0.07 | 0.14 | 0.06 | 0.02 | 0.18 | 0.07 |
| P_18:0 LPC | 33.04 | 508.4 | 0.01 | 0.01 | 0.01 | 0.01 | 0.07 | 0.06 | 0.01 |
| 18:2 LPC | 25.43 | 520.4 | 0.02 | 0.04 | 0.06 | 0.03 | 0.02 | 0.08 | 0.14 |
| 18:1 LPC | 29.26 | 522.4 | 0.83 | 1.11 | 2.08 | 0.84 | 1.09 | 2.80 | 1.23 |
| 18:0 LPC | 34.51 | 524.4 | 0.50 | 0.94 | 1.06 | 0.83 | 0.35 | 0.52 | 0.47 |
| 20:5 LPC | 22.62 | 542.4 | 0.22 | 1.98 | 0.57 | 0.20 | 0.14 | 2.05 | 0.37 |
| 20:4 LPC | 25.51 | 544.4 | 0.15 | 0.13 | 0.69 | 0.31 | 0.06 | 0.10 | 0.08 |
| 20:3 LPC | 28.21 | 546.4 | 0.01 | 0.01 | 0.02 | 0.01 | 0.01 | 0.01 | 0.02 |
| 20:1 LPC | 35.67 | 550.4 | 0.02 | 0.12 | 0.01 | 0.02 | 0.02 | 0.19 | 0.04 |
| 22:6 LPC | 25.59 | 568.4 | 0.95 | 2.62 | 1.82 | 0.68 | 0.38 | 1.89 | 0.54 |
| 22:5 LPC iso | 27.51 | 570.4 | 0.06 | 0.24 | 0.03 | 0.04 | 0.01 | 0.08 | 0.04 |
| 22:5 LPC | 28.64 | 570.4 | 0.04 | 0.01 | 0.13 | 0.04 | 0.01 | 0.02 | 0.03 |
| | | Sum | 5.49 | 10.66 | 12.29 | 7.67 | 4.10 | 12.77 | 6.94 |

TABLE 16

The concentration of PCs in seven species of fish roe extracts

| | | | Concentration, mg/g | | | | | | |
|---|---|---|---|---|---|---|---|---|---|
| PC | $t_R$, min | $[M + H]^+$ | HAM | SAL | TUN | MOS | SEV | LUM | BOR |
| 16:0_14:0 PC | 57.62 | 706.5 | 1.5 | 0.1 | 1.1 | 1.2 | 0.2 | 0.0 | 0.7 |
| 16:1_16:1 PC | 54.34 | 730.5 | 0.4 | 0.1 | 0.0 | 0.1 | 0.0 | 0.0 | 0.1 |
| 14:0_18:2 PC | 57.67 | 730.5 | 0.2 | 0.1 | 0.0 | 0.0 | 0.0 | 0.0 | 0.0 |
| 16:0_16:1 PC | 58.81 | 732.5 | 6.6 | 1.6 | 3.5 | 3.2 | 1.3 | 0.6 | 2.8 |
| 16:0_16:0 PC | 63.80 | 734.5 | 1.5 | 0.1 | 3.0 | 2.2 | 0.4 | 0.1 | 1.2 |
| 15:0_18:2 PC | 58.49 | 744.5 | 0.3 | 0.1 | 0.0 | 0.1 | 0.0 | 0.0 | 0.0 |
| P-18:0_16:0 PC | 63.19 | 746.5 | 1.6 | 0.3 | 0.3 | 0.0 | 0.1 | 0.0 | 0.8 |
| 14:0_20:5 PC | 52.04 | 752.6 | 0.3 | 5.3 | 0.2 | 0.1 | 0.0 | 0.1 | 0.1 |
| 16:1_18:4 PC | 54.51 | 752.6 | 0.0 | 0.0 | 0.0 | 0.0 | 0.0 | 0.0 | 0.0 |
| 16:0_18:4 PC | 58.81 | 754.5 | 0.5 | 0.1 | 0.3 | 0.2 | 0.1 | 0.0 | 0.2 |
| 16:1_18:2 PC | 57.32 | 756.5 | 0.1 | 0.0 | 0.0 | 0.0 | 0.0 | 0.0 | 0.1 |
| 16:0_18:3 PC | 58.38 | 756.5 | 0.2 | 0.2 | 0.1 | 0.2 | 0.2 | 0.0 | 0.5 |
| 16:1_18:1 PC | 61.18 | 758.5 | 2.1 | 0.7 | 0.3 | 0.4 | 0.5 | 0.1 | 0.3 |

TABLE 16-continued

The concentration of PCs in seven species of fish roe extracts

| | | | Concentration, mg/g | | | | | | |
|---|---|---|---|---|---|---|---|---|---|
| PC | $t_R$, min | $[M + H]^+$ | HAM | SAL | TUN | MOS | SEV | LUM | BOR |
| 16:0_18:2 PC | 62.06 | 758.5 | 1.6 | 0.3 | 1.2 | 1.6 | 1.3 | 0.4 | 2.2 |
| 16:0_18:1 PC | 65.78 | 760.5 | 14.9 | 5.3 | 10.4 | 14.2 | 11.8 | 3.1 | 10.5 |
| 18:0_16:0 PC | 71.31 | 762.5 | 2.4 | 0.6 | 0.3 | 0.4 | 0.0 | 0.0 | 0.1 |
| 15:0_20:5 PC | 53.89 | 766.5 | 0.0 | 0.2 | 0.1 | 0.3 | 0.5 | 0.3 | 0.6 |
| 15:1_20:4 PC | 54.88 | 766.5 | 0.1 | 0.5 | 0.0 | 0.2 | 0.0 | 0.0 | 0.0 |
| 15:0_20:4 PC | 64.56 | 768.5 | 0.4 | 0.0 | 0.1 | 0.7 | 0.2 | 0.0 | 0.2 |
| P20:0_14:0 PC | 68.19 | 774.5 | 0.0 | 0.7 | 0.0 | 0.0 | 0.0 | 0.0 | 0.0 |
| 17:0_18:1 PC | 69.20 | 774.5 | 0.6 | 0.1 | 0.2 | 0.5 | 0.1 | 0.0 | 0.2 |
| 16:1_20:5 PC | 53.23 | 778.5 | 0.6 | 1.2 | 0.1 | 0.1 | 0.1 | 0.1 | 0.2 |
| 22:6_14:0 PC | 54.70 | 778.5 | 0.7 | 6.5 | 0.5 | 0.3 | 0.1 | 0.2 | 0.1 |
| 14:0_22:5 PC | 56.66 | 780.5 | 0.5 | 1.1 | 0.1 | 0.1 | 0.1 | 0.0 | 0.1 |
| 16:0_20:5 PC | 57.82 | 780.5 | 8.0 | 8.7 | 4.9 | 4.4 | 4.6 | 3.7 | 3.2 |
| 14:0_22:4 PC | 59.74 | 782.5 | 0.1 | 0.2 | 0.0 | 0.1 | 0.0 | 0.0 | 0.0 |
| 16:0_20:4 PC | 61.08 | 782.5 | 5.0 | 0.5 | 4.2 | 6.9 | 1.4 | 0.1 | 0.6 |
| 18:3_18:1 PC | 65.84 | 782.5 | 1.6 | 0.4 | 1.0 | 1.4 | 1.2 | 0.3 | 0.9 |
| 18:1_18:2 PC | 63.34 | 784.5 | 0.2 | 0.2 | 0.1 | 0.1 | 0.3 | 0.0 | 0.2 |
| 16:0_20:3 PC | 63.95 | 784.5 | 0.2 | 0.1 | 0.2 | 0.3 | 0.3 | 0.1 | 0.0 |
| 18:0_18:3 PC | 65.81 | 784.5 | 0.1 | 0.0 | 0.1 | 0.1 | 0.2 | 0.0 | 0.1 |
| 16:0_20:2 PC | 67.01 | 786.5 | 1.7 | 1.7 | 0.3 | 0.5 | 1.1 | 0.5 | 0.5 |
| 18:1_18:1 PC | 68.13 | 786.5 | 0.2 | 0.3 | 0.1 | 0.3 | 0.1 | 0.0 | 0.6 |
| 18:0_18:2 PC | 69.76 | 786.5 | 0.3 | 0.1 | 0.0 | 0.1 | 0.0 | 0.1 | 0.1 |
| 18:0_18:1 PC | 71.80 | 788.5 | 6.8 | 2.3 | 1.0 | 2.6 | 1.5 | 0.3 | 0.8 |
| 15:0_22:6 PC | 57.54 | 792.5 | 1.0 | 0.7 | 0.2 | 0.2 | 0.0 | 0.1 | 0.1 |
| P16:0_22:6 PC | 64.32 | 792.5 | 1.5 | 0.4 | 0.3 | 1.8 | 0.8 | 0.3 | 0.9 |
| 17:0_20:4 PC | 64.30 | 796.5 | 0.2 | 0.0 | 0.1 | 0.2 | 0.0 | 0.0 | 0.0 |
| 16:1_22:6 PC | 55.96 | 804.6 | 1.2 | 11.5 | 0.4 | 0.3 | 0.1 | 0.1 | 0.1 |
| 18:1_20:5 PC | 58.16 | 806.6 | 2.2 | 6.3 | 0.4 | 0.4 | 1.1 | 1.8 | 0.5 |
| 16:0_22:6 PC | 59.59 | 806.6 | 11.8 | 8.3 | 9.2 | 10.4 | 6.9 | 3.7 | 4.4 |
| 18:1_20:4 PC | 59.47 | 808.6 | 0.0 | 0.0 | 0.6 | 1.7 | 0.8 | 0.4 | 0.8 |
| 16:0_22:5 PC | 61.62 | 808.6 | 4.9 | 6.5 | 2.2 | 3.0 | 1.3 | 0.8 | 1.6 |
| 18:0_20:5 PC | 62.69 | 808.6 | 5.2 | 10.4 | 0.0 | 0.0 | 0.1 | 0.0 | 0.0 |
| 18:1_20:3 PC | 65.72 | 810.6 | 0.4 | 0.0 | 0.3 | 0.0 | 0.0 | 0.0 | 0.1 |
| 16:0_22:4 PC | 67.21 | 810.6 | 2.6 | 0.5 | 0.7 | 2.3 | 0.6 | 0.1 | 0.3 |
| 18:0_20:4 PC | 71.72 | 810.6 | 0.5 | 0.3 | 0.0 | 0.1 | 0.1 | 0.0 | 0.0 |
| 18:1_20:2 PC | 68.98 | 812.6 | 0.1 | 0.0 | 0.0 | 0.0 | 0.0 | 0.0 | 0.1 |
| 18:0_20:3 PC | 69.88 | 812.6 | 0.1 | 0.0 | 0.0 | 0.1 | 0.0 | 0.0 | 0.0 |
| 18:2_20:1 PC | 71.58 | 812.6 | 0.1 | 0.0 | 0.0 | 0.0 | 0.1 | 0.0 | 0.0 |
| 18:1_20:1 PC | 72.61 | 814.6 | 0.1 | 0.9 | 0.0 | 0.1 | 0.1 | 0.1 | 0.0 |
| P-18:0_22:6 PC | 58.87 | 818.6 | 0.9 | 3.2 | 0.3 | 0.2 | 0.1 | 0.3 | 0.1 |
| 18:0_20:0 PC | 65.16 | 818.6 | 0.1 | 0.1 | 0.0 | 0.1 | 1.1 | 0.1 | 0.0 |
| 22:6_17:0 PC | 62.63 | 820.6 | 0.3 | 0.2 | 0.1 | 0.1 | 0.0 | 0.1 | 0.2 |
| 17:0_22:6 PC | 63.54 | 820.6 | 0.6 | 0.5 | 0.2 | 0.4 | 0.1 | 0.1 | 0.1 |
| 22:6_18:3 PC | 58.94 | 828.6 | 0.2 | 0.7 | 0.1 | 0.0 | 0.1 | 0.2 | 0.0 |
| 18:3_22:6 PC | 60.31 | 828.6 | 1.5 | 2.2 | 1.0 | 1.2 | 0.7 | 0.3 | 0.3 |
| 20:4_20:4 PC | 62.50 | 830.6 | 0.4 | 0.3 | 0.1 | 0.2 | 0.1 | 0.0 | 0.1 |
| 21:0_18:1 PC | 63.86 | 830.6 | 0.4 | 0.8 | 0.2 | 0.3 | 0.1 | 0.1 | 0.1 |
| 21:0_18:0 PC | 60.75 | 832.6 | 6.4 | 13.9 | 1.5 | 1.4 | 3.0 | 2.3 | 0.9 |
| 18:1_22:5 PC | 63.63 | 834.6 | 0.6 | 2.4 | 0.1 | 0.1 | 0.1 | 0.1 | 0.1 |
| 18:2_22:4 PC | 65.08 | 834.6 | 0.6 | 3.9 | 0.1 | 0.2 | 0.3 | 0.3 | 0.2 |
| 18:0_22:6 PC | 66.87 | 834.6 | 7.5 | 12.6 | 2.2 | 3.0 | 2.0 | 0.5 | 0.9 |
| 18:0_22:5 PC | 68.56 | 836.6 | 0.9 | 4.0 | 0.1 | 0.2 | 0.1 | 0.0 | 0.1 |
| 18:1_22:4 PC | 69.78 | 836.6 | 0.4 | 0.5 | 0.2 | 0.3 | 0.0 | 0.0 | 0.1 |
| 18:0_22:4 PC | 71.54 | 838.6 | 0.2 | 0.0 | 0.0 | 0.1 | 0.0 | 0.0 | 0.0 |
| | | Sum | 114.2 | 130.9 | 54.0 | 71.6 | 47.9 | 22.3 | 40.1 |

TABLE 17

The concentration of LPEs in seven species of fish roe extracts

| | | | Concentration, mg/g | | | | | | |
|---|---|---|---|---|---|---|---|---|---|
| LPE | $t_R$, min | $[M + H]^+$ | HAM | SAL | TUN | MOS | SEV | LUM | BOR |
| 14:0 LPE | 12.80 | 426.4 | 0.00 | 0.00 | 0.00 | 0.00 | 0.00 | 0.00 | 0.00 |
| 15:0 LPE | 23.21 | 440.4 | 0.17 | 0.22 | 0.17 | 0.25 | 0.25 | 0.19 | 0.69 |
| 16:1 LPE | 17.25 | 452.4 | 0.40 | 0.54 | 0.43 | 0.51 | 0.48 | 0.47 | 0.46 |
| 16:0 LPE | 14.13 | 454.4 | 0.14 | 0.63 | 0.32 | 0.26 | 0.18 | 0.42 | 0.10 |
| 17:0 LPE | 13.20 | 468.4 | 1.55 | 2.09 | 1.60 | 1.58 | 1.55 | 1.62 | 1.60 |
| O-18:0 LPE | 19.76 | 468.4 | 0.00 | 0.00 | 0.00 | 0.00 | 0.00 | 0.00 | 0.92 |

TABLE 17-continued

The concentration of LPEs in seven species of fish roe extracts

| LPE | $t_R$, min | $[M + H]^+$ | Concentration, mg/g | | | | | | |
|---|---|---|---|---|---|---|---|---|---|
| | | | HAM | SAL | TUN | MOS | SEV | LUM | BOR |
| 18:4 LPE | 14.24 | 474.4 | 0.12 | 0.08 | 0.03 | 0.14 | 0.14 | 0.13 | 0.12 |
| 18:3 LPE | 14.23 | 476.4 | 0.05 | 0.28 | 0.07 | 0.06 | 0.11 | 0.11 | 0.05 |
| 18:2 LPE | 27.45 | 478.4 | 0.00 | 0.00 | 0.25 | 0.00 | 0.00 | 0.16 | 0.08 |
| 18:1 LPE | 28.01 | 480.4 | 0.00 | 0.00 | 0.39 | 0.76 | 0.00 | 1.02 | 0.28 |
| 18:0 LPE | 16.64 | 482.4 | 0.15 | 1.00 | 0.26 | 0.20 | 0.20 | 0.33 | 0.21 |
| 20:5 LPE | 13.08 | 500.4 | 0.02 | 0.15 | 0.00 | 0.00 | 0.04 | 0.17 | 0.03 |
| 20:3 LPE | 17.05 | 504.4 | 0.16 | 0.62 | 0.34 | 0.25 | 0.35 | 0.35 | 0.31 |
| 20:1 LPE | 26.25 | 508.4 | 1.01 | 0.84 | 2.47 | 1.01 | 0.30 | 3.12 | 1.15 |
| 22:6 LPE | 13.87 | 526.4 | 0.12 | 0.24 | 0.22 | 0.07 | 0.11 | 0.25 | 0.08 |
| 22:5 LPE | 23.97 | 528.4 | 0.12 | 0.17 | 0.10 | 0.12 | 0.12 | 0.12 | 0.11 |
| Sum | | | 4.02 | 6.85 | 6.66 | 5.20 | 3.85 | 8.46 | 6.19 |

The total amount of PEs was found the highest in SAL (21.1 mg/g), followed by HAM (16.1 mg/mL), as shown in TABLE 18. The sum of PEs containing DHA esterified in SAL and HAM were 9.8 and 7.1 mg/g, respectively. The sum of PEs containing EPA esterified in SAL (1.8), and HAM was and 1.5 mg/g, respectively. The concentration of 18:0_22:6 PE, 16:0_22:6 PE, and 18:1_22:6 PE was relatively high in SAL followed by HAM. The amount of 18:0_22:6 PE, 16:0_22:6 PE, and 18:1_22:6 PE in SAL were, 2.1, 2.1, 1.5 mg/g and 1.5, 1.7, 1.2 mg/g in HAM, respectively.

TABLE 18

The concentration of PEs in seven species of fish roe extracts

| PE | $t_R$, min | $[M + M]^+$ | Concentration, mg/g | | | | | | |
|---|---|---|---|---|---|---|---|---|---|
| | | | HAM | SAL | TUN | MOS | SEV | LUM | BOR |
| 16:0_18:2 PE | 37.94 | 716.5 | 0.17 | 0.21 | 0.00 | 0.00 | 0.00 | 0.00 | 0.00 |
| 16:0_18:1 PE | 40.77 | 718.5 | 0.32 | 0.39 | 0.02 | 0.04 | 0.04 | 0.01 | 0.01 |
| P16:0_20:4 PE | 18.12 | 724.5 | 0.93 | 1.13 | 0.06 | 0.08 | 0.07 | 0.06 | 0.06 |
| 16:0_20:5 PE | 36.17 | 738.5 | 0.30 | 0.36 | 0.04 | 0.09 | 0.08 | 0.03 | 0.02 |
| 16:0 20:4 PE | 38.28 | 740.5 | 0.54 | 0.65 | 0.12 | 0.37 | 1.45 | 0.10 | 0.22 |
| P15:1_22:6 PE | 39.49 | 748.5 | 0.90 | 1.09 | 0.21 | 0.27 | 0.29 | 0.00 | 0.04 |
| P16:0_22:5 PE | 39.48 | 750.5 | 0.10 | 0.12 | 0.02 | 0.03 | 0.05 | 0.00 | 0.00 |
| P18:0_20:5 PE | 40.68 | 750.5 | 0.17 | 0.20 | 0.03 | 0.05 | 0.23 | 0.00 | 0.06 |
| P18:0_20:4 PE | 37.68 | 752.5 | 0.36 | 0.43 | 0.00 | 0.00 | 0.06 | 0.03 | 0.06 |
| P16:0_22:4 PE | 39.89 | 752.5 | 0.35 | 0.42 | 0.00 | 0.00 | 0.19 | 0.20 | 0.02 |
| 16:0_22:6 PE | 38.24 | 764.5 | 1.71 | 2.06 | 0.45 | 0.94 | 0.28 | 0.10 | 0.11 |
| 18:1_20:4 PE | 39.30 | 766.5 | 0.57 | 0.69 | 0.06 | 0.09 | 0.23 | 0.06 | 0.04 |
| 18:0_20:5 PE | 40.26 | 766.5 | 0.99 | 1.20 | 0.17 | 0.35 | 0.54 | 0.12 | 0.10 |
| 18:0_20:4 PE iso | 41.07 | 768.5 | 0.24 | 0.28 | 0.03 | 0.08 | 1.31 | 0.13 | 0.30 |
| 18:0_20:4 PE | 42.25 | 768.5 | 1.04 | 1.26 | 0.15 | 0.59 | 0.46 | 0.02 | 0.05 |
| 16.0_22:1 PE | 46.94 | 774.5 | 0.22 | 0.26 | 0.20 | 0.26 | 0.24 | 0.06 | 0.70 |
| P22:5_18:0 PE | 48.67 | 776.5 | 1.04 | 1.26 | 1.62 | 2.57 | 1.18 | 0.18 | 3.06 |
| O-18:0_22:6 PE | 44.19 | 778.5 | 0.20 | 0.24 | 0.05 | 0.02 | 0.04 | 0.02 | 0.02 |
| 18:3_22:6 PE | 38.20 | 786.5 | 0.70 | 0.85 | 0.16 | 0.31 | 0.07 | 0.02 | 0.04 |
| 18:1_22:6 PE | 39.16 | 790.5 | 1.23 | 1.49 | 0.26 | 0.17 | 0.48 | 0.22 | 0.05 |
| 18:2_22:4 PE | 41.57 | 792.5 | 0.09 | 0.59 | 0.09 | 0.00 | 0.00 | 0.04 | 0.06 |
| 22:6_18:0 PE | 42.25 | 792.5 | 0.11 | 1.11 | 0.05 | 0.00 | 0.00 | 0.02 | 0.06 |
| 18:0_22:6 PE | 43.21 | 792.5 | 1.54 | 2.11 | 0.53 | 0.78 | 0.74 | 0.18 | 0.27 |
| 22:5_18:0 PE | 43.06 | 794.5 | 0.29 | 0.35 | 0.04 | 0.00 | 0.10 | 0.00 | 0.03 |
| 18.0_22:5 PE | 43.68 | 794.5 | 0.21 | 0.26 | 0.09 | 0.12 | 0.03 | 0.00 | 0.05 |
| 18.0_22:4 PE | 46.20 | 796.5 | 0.83 | 1.00 | 0.55 | 0.37 | 0.65 | 0.00 | 0.62 |
| 18:0_22:5 PE | 48.73 | 808.5 | 0.03 | 0.03 | 0.00 | 0.00 | 0.00 | 0.00 | 0.00 |
| 18:0_22:4 PE | 50.07 | 808.5 | 0.22 | 0.27 | 0.00 | 0.00 | 0.00 | 0.00 | 0.00 |
| 20.3_22:6 PE | 44.85 | 814.5 | 0.66 | 0.80 | 0.15 | 0.20 | 0.19 | 0.03 | 0.05 |
| Sum | | | 16.06 | 21.14 | 5.17 | 7.78 | 9.00 | 1.64 | 6.07 |

It is to be understood that this invention is not limited to any particular embodiment described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order, which is logically possible.

REFERENCES

1. Ahmmed, M. K.; Ahmmed, F.; Tian, H.; Came, A.; Bekhit, A. E.-D., Marine omega-3 (n-3) phospholipids: A comprehensive review of their properties, sources, bioavailability, and relation to brain health. *Comprehensive Reviews in Food Science and Food Safety* 2020, 19, (1), 64-123.
2. Depeint, F.; Bruce, W. R.; Shangari, N.; Mehta, R.; O'Brien, P. J., Mitochondrial function and toxicity: role of the B vitamin family on mitochondrial energy metabolism. *Chemico-biological interactions* 2006, 163, (1-2), 94-112.
3. Narciso, L.; Parlanti, E.; Racaniello, M.; Simonelli, V.; Cardinale, A.; Merlo, D.; Dogliotti, E., The Response to Oxidative DNA Damage in Neurons: Mechanisms and Disease. *Neural Plasticity* 2016, 2016, 3619274.
4. Polosina, Y., DNA Repair☆. In *Reference Module in Biomedical Sciences*, Elsevier: 2014.
5. Kronenberg, G.; Harms, C.; Sobol, R. W.; Cardozo-Pelaez, F.; Linhart, H.; Winter, B.; Balkaya, M.; Gertz, K.; Gay, S. B.; Cox, D.; Eckart, S.; Ahmadi, M.; Juckel, G.; Kempermann, G.; Hellweg, R.; Sohr, R.; Hörtnagl, H.; Wilson, S. H.; Jaenisch, R.; Endres, M., Folate Deficiency Induces Neurodegeneration and Brain Dysfunction in Mice Lacking Uracil DNA Glycosylase. *The Journal of Neuroscience* 2008, 28, (28), 7219.
6. Dizdaroglu, M.; Karakaya, A.; Jaruga, P.; Slupphaug, G.; Krokan, H. E., Novel activities of human uracil DNA N-glycosylase for cytosine-derived products of oxidative DNA damage. *Nucleic acids research* 1996, 24, (3), 418-22.
7. Fujimoto, J.; Tran, L.; Sowers, L. C., Synthesis and cleavage of oligodeoxynucleotides containing a 5-hydroxyuracil residue at a defined site. *Chemical research in toxicology* 1997, 10, (11), 1254-8.
8. Kavli, B.; Sundheim, O.; Akbari, M.; Otterlei, M.; Nilsen, H.; Skorpen, F.; Aas, P. A.; Hagen, L.; Krokan, H. E.; Slupphaug, G., hUNG2 is the major repair enzyme for removal of uracil from U:A matches, U:G mismatches, and U in single-stranded DNA, with hSMUG1 as a broad specificity backup. *The Journal of biological chemistry* 2002, 277, (42), 39926-36.
9. Torres, R. J.; Prior, C.; Garcia, M. G.; Puig, J. G., A review of the implication of hypoxanthine excess in the physiopathology of Lesch-Nyhan disease. *Nucleosides, nucleotides & nucleic acids* 2016, 35, (10-12), 507-516.
10. Growdon, J. H., Use of Phosphatidylcholine in Brain Diseases: An Overview. In *Lecithin: Technological, Biological, and Therapeutic Aspects*, Hanin, I.; Ansell, G. B., Eds. Springer US: Boston, Mass., 1987; pp 121-136.
11. Hirsch, M. J.; Wurtman, R. J., Lecithin consumption increases acetylcholine concentrations in rat brain and adrenal gland. *Science (New York, N.Y.)* 1978, 202, (4364), 223-5.
12. Cohen, E. L.; Wurtman, R. J., Brain acetylcholine: Increase after systematic choline administration. *Life Sciences* 1975, 16, (7), 1095-1102.
13. Growdon, J. H.; Gelenberg, A. J.; Doller, J.; Hirsch, M. J.; Wurtman, R. J., Lecithin can suppress tardive dyskinesia. *The New England journal of medicine* 1978, 298, (18), 1029-30.
14. Growdon, J. H.; Wheeler, S.; Graham, H. N., Plasma choline responses to lecithin-enriched soup. *Psychopharmacology bulletin* 1984, 20, (3), 603-6.
15. Bjelland, I.; Tell, G. S.; Vollset, S. E.; Konstantinova, S.; Ueland, P. M., Choline in anxiety and depression: the Hordaland Health Study. *The American Journal of Clinical Nutrition* 2009, 90, (4), 1056-1060.
16. Rao, S.; Lam, M. H.; Wing, Y. K.; Yim, L. C.; Chu, W. C.; Yeung, V. S.; Waye, M. M., Beneficial effect of phosphatidylcholine supplementation in alleviation of hypomania and insomnia in a Chinese bipolar hypomanic boy and a possible explanation to the effect at the genetic level. *SpringerPlus* 2015, 4, 235.
17. Hallaraker, H.; Remmereit, J.; Berger, A. Lipid compositions with high DHA content. U.S. Pat. No. 8,846,604 B2, 2014.
18. Folch, J.; Lees, M.; Sloane Stanley, G. H., A simple method for the isolation and purification of total lipids from animal tissues. *The Journal of biological chemistry* 1957, 226, (1), 497-509.
19. Folch, J.; Lees, M.; Stanley, G. H. S., A simple method for the isolation and purification of total lipids from animal tissues. *Journal of Biological Chemistry* 1957, 226, 497-509.
20. Bligh, E. G.; Dyer, W. J., A rapid method of total lipid extraction and purification. *Canadian journal of biochemistry and physiology* 1959, 37, (8), 911-7.
21. Hara, A.; Radin, N. S., Lipid extraction of tissues with a low-toxicity solvent. *Analytical biochemistry* 1978, 90, (1), 420-6.

22. Tanaka, Y.; Sakaki, I.; Ohkubo, T., Extraction of Phospholipids from Salmon Roe with Supercritical Carbon Dioxide and an Entrainer. *Journal of oleo science* 2004, 53, (9), 417-424.
23. Khedr, A.; Alahdal, A. M., Optimized Gas Chromatography-Mass Spectrometric Method to Profile Esterified Fatty Acids in Fish Roe and Fish Oil. *Indian J. Pharm. Sci.* 2018, 80, (4), 628-636.
24. Khedr, A.; Khayat, M. T.; Khayyat, A. N., A new approach for characterization of phosphatidylcholines and lysophosphatidylcholine in human plasma. *Bioanalysis* 2020, 12, (3), 191-204.
25. Khedr, A.; Hegazy, M. A.; Kammoun, A. K.; Shehata, M. A., Phospholipidomic identification of potential serum biomarkers in dengue fever, hepatitis B and hepatitis C using liquid chromatography-electrospray ionization-tandem mass spectrometry. *Journal of chromatography. B, Analytical technologies in the biomedical and life sciences* 2015, 1009-1010, 44-54.

What is claimed is:

1. A method for extracting one or more phospholipids, comprising:
    collecting and freezing fish roe;
    drying and grinding the fish roe to form a fish roe powder;
    blending the fish roe powder with a solvent to extract the one or more phospholipids, wherein the solvent comprises a mixture of chloroform, ethanol and isopropanol; and
    drying the one or more phospholipids, wherein the one or more phospholipids have at least one omega-3 fatty acid moiety, wherein the at least one omega-3 fatty acid moiety is docosahexaenoic acid (DHA) and/or eicosapentaenoic acid (EPA).
2. The method of claim 1, wherein the fish roe is frozen at −80° C. for 12-24 hours.
3. The method of claim 1, wherein the fish roe is dried in a lyophilizer at 0.05-0.01 mbar.
4. The method of claim 1, wherein the solvent comprises 15-35 v/v % of ethanol.
5. The method of claim 1, wherein the solvent comprises 30-65 v/v % of chloroform.
6. The method of claim 1, wherein the solvent comprises 10-25% of isopropanol.
7. The method of claim 1, wherein the mixture of chloroform, ethanol and isopropanol is at a 2:1:0.5 v/v ratio.
8. The method of claim 1, wherein the solvent does not contain methanol.
9. The method of claim 1, wherein the solvent does not contain water.
10. The method of claim 1, wherein the one or more phospholipids are not washed in an aqueous solution.
11. The method of claim 1, wherein the fish roe is selected from the group consisting of hamour roe, salmon roe, tuna roe, mosa roe, sevruga sturgeon roe, lump roe, bory roe and combinations thereof.
12. The method of claim 1, wherein the fish roe is salmon roe.
13. The method of claim 1, wherein the fish roe is hamour roe.

* * * * *